(12) United States Patent
Stein et al.

(10) Patent No.: US 10,492,924 B2
(45) Date of Patent: Dec. 3, 2019

(54) LORDOTIC EXPANDABLE INTERBODY IMPLANT

(71) Applicant: NuVasive, Inc., San Diego, CA (US)

(72) Inventors: Christopher Stein, Fallbrook, CA (US); Seth Gustine, Encinitas, CA (US)

(73) Assignee: NuVasive, Inc., San Diego, CA (US)

(*) Notice: Subject to any disclaimer, the term of this patent is extended or adjusted under 35 U.S.C. 154(b) by 0 days.

(21) Appl. No.: 15/799,554

(22) Filed: Oct. 31, 2017

(65) Prior Publication Data

US 2018/0064551 A1 Mar. 8, 2018

Related U.S. Application Data

(63) Continuation of application No. 14/456,640, filed on Aug. 11, 2014, now Pat. No. 9,801,734.

(60) Provisional application No. 61/864,132, filed on Aug. 9, 2013.

(51) Int. Cl.
*A61F 2/44* (2006.01)
*A61F 2/30* (2006.01)

(52) U.S. Cl.
CPC .... *A61F 2/447* (2013.01); *A61F 2002/30158* (2013.01); *A61F 2002/30387* (2013.01); *A61F 2002/30471* (2013.01); *A61F 2002/30507* (2013.01); *A61F 2002/30538* (2013.01); *A61F 2002/30904* (2013.01)

(58) Field of Classification Search
CPC ..................................... A61F 2/4455
USPC ....................................... 623/17.11
See application file for complete search history.

(56) References Cited

U.S. PATENT DOCUMENTS

| 4,759,769 | A | 7/1988 | Hedman et al. |
| 4,863,476 | A | 9/1989 | Shepperd |
| 5,554,191 | A | 9/1996 | Lahille et al. |
| 5,653,763 | A | 8/1997 | Errico et al. |
| 5,658,335 | A | 8/1997 | Allen |
| 5,665,122 | A | 9/1997 | Kambin |
| 5,669,909 | A | 9/1997 | Zdeblick et al. |
| D390,592 | S | 2/1998 | Agata |
| 5,776,199 | A | 7/1998 | Michelson |
| 5,782,832 | A | 7/1998 | Larsen et al. |
| 5,782,919 | A | 7/1998 | Zdeblick et al. |
| D397,439 | S | 8/1998 | Koros et al. |
| 5,865,848 | A | 2/1999 | Baker |
| 5,893,889 | A | 4/1999 | Harrington |
| 5,935,129 | A | 8/1999 | McDevitt et al. |
| 5,980,522 | A | 11/1999 | Koros et al. |
| 6,045,579 | A | 4/2000 | Hochshuler et al. |

(Continued)

FOREIGN PATENT DOCUMENTS

| AU | 765774 | 3/2002 |
| AU | 2004100977 | 12/2004 |

(Continued)

OTHER PUBLICATIONS

U.S. Appl. No. 14/285,590, Stein.

*Primary Examiner* — David W Bates

(57) ABSTRACT

An expandable spinal fusion implant including a housing, upper and lower endplates, a wedge positioned within the housing and between the upper and lower endplates and a drive mechanism to urge the wedge distally between the upper and lower endplates to increase the separation between the endplates and expand the overall height of the distal end of the implant.

20 Claims, 18 Drawing Sheets

(56) References Cited

U.S. PATENT DOCUMENTS

| | | | |
|---|---|---|---|
| 6,080,193 A | 6/2000 | Hochshuler et al. | |
| 6,102,950 A | 8/2000 | Vaccaro | |
| 6,117,174 A | 9/2000 | Nolan | |
| 6,129,763 A | 10/2000 | Chauvin et al. | |
| 6,176,882 B1 * | 1/2001 | Biedermann | A61F 2/447 623/17.11 |
| 6,179,873 B1 | 1/2001 | Zientek | |
| 6,190,414 B1 | 2/2001 | Young et al. | |
| 6,214,050 B1 | 4/2001 | Huene | |
| 6,217,579 B1 | 4/2001 | Koros | |
| 6,302,914 B1 | 10/2001 | Michelson | |
| H2009 H | 1/2002 | Martin et al. | |
| 6,340,369 B1 | 1/2002 | Ferree | |
| 6,344,058 B1 | 2/2002 | Ferree | |
| 6,350,126 B1 | 2/2002 | Levisman | |
| 6,352,557 B1 | 3/2002 | Ferree | |
| 6,355,069 B1 | 3/2002 | DeCarlo, Jr. et al. | |
| 6,368,351 B1 | 4/2002 | Glenn et al. | |
| 6,371,989 B1 | 4/2002 | Chauvin et al. | |
| 6,375,655 B1 | 4/2002 | Zdeblick et al. | |
| 6,419,702 B1 | 7/2002 | Ferree | |
| 6,436,140 B1 | 8/2002 | Liu et al. | |
| 6,436,142 B1 | 8/2002 | Paes et al. | |
| 6,443,989 B1 | 9/2002 | Jackson | |
| 6,443,990 B1 | 9/2002 | Aebi et al. | |
| 6,447,544 B1 | 9/2002 | Michelson | |
| 6,447,547 B1 | 9/2002 | Michelson | |
| 6,451,057 B1 | 9/2002 | Chen et al. | |
| 6,454,806 B1 | 9/2002 | Cohen et al. | |
| 6,454,807 B1 | 9/2002 | Jackson | |
| 6,471,724 B2 | 10/2002 | Zdeblick et al. | |
| 6,478,823 B1 | 11/2002 | Michelson | |
| 6,491,724 B1 | 12/2002 | Ferree | |
| 6,506,051 B2 | 1/2003 | Levisman | |
| 6,520,991 B2 | 2/2003 | Huene | |
| 6,533,791 B1 | 3/2003 | Betz et al. | |
| 6,562,074 B2 | 5/2003 | Gerbec et al. | |
| 6,576,016 B1 | 6/2003 | Hochshuler et al. | |
| 6,579,290 B1 | 6/2003 | Hardcastle et al. | |
| 6,613,091 B1 | 9/2003 | Zdeblick et al. | |
| 6,613,093 B2 | 9/2003 | DeCarlo, Jr. et al. | |
| 6,641,614 B1 * | 11/2003 | Wagner | A61F 2/4455 623/17.15 |
| 6,645,206 B1 | 11/2003 | Zdeblick et al. | |
| 6,648,917 B2 | 11/2003 | Gerbec et al. | |
| 6,648,918 B2 | 11/2003 | Ferree | |
| 6,666,891 B2 | 12/2003 | Boehm, Jr. et al. | |
| 6,685,742 B1 | 2/2004 | Jackson | |
| 6,695,851 B2 | 2/2004 | Zdeblick et al. | |
| 6,706,070 B1 | 3/2004 | Wagner et al. | |
| 6,719,796 B2 | 4/2004 | Cohen et al. | |
| 6,719,797 B1 | 4/2004 | Ferree | |
| 6,730,126 B2 | 5/2004 | Boehm, Jr. et al. | |
| 6,733,535 B2 | 5/2004 | Michelson | |
| 6,743,255 B2 | 6/2004 | Ferree | |
| 6,773,460 B2 | 8/2004 | Jackson | |
| 6,821,298 B1 | 11/2004 | Jackson | |
| 6,835,206 B2 | 12/2004 | Jackson | |
| 6,852,129 B2 | 2/2005 | Gerbec et al. | |
| 6,863,673 B2 | 3/2005 | Gerbec et al. | |
| 6,905,512 B2 | 6/2005 | Paes et al. | |
| 6,955,691 B2 | 10/2005 | Chae et al. | |
| 7,066,961 B2 | 6/2006 | Michelson | |
| 7,070,598 B2 | 7/2006 | Lim et al. | |
| 7,087,055 B2 | 8/2006 | Lim et al. | |
| 7,128,760 B2 | 10/2006 | Michelson | |
| 7,156,874 B2 | 1/2007 | Paponneau et al. | |
| 7,204,853 B2 | 4/2007 | Gordon et al. | |
| 7,211,112 B2 | 5/2007 | Baynham et al. | |
| 7,217,291 B2 | 5/2007 | Zucherman et al. | |
| 7,217,293 B2 | 5/2007 | Branch, Jr. | |
| 7,220,280 B2 | 5/2007 | Kast et al. | |
| 7,238,186 B2 | 7/2007 | Zdeblick et al. | |
| 7,282,063 B2 | 10/2007 | Cohen et al. | |
| 7,316,714 B2 | 1/2008 | Gordon et al. | |
| 7,410,501 B2 | 8/2008 | Michelson | |
| 7,431,735 B2 | 10/2008 | Liu et al. | |
| 7,445,636 B2 | 11/2008 | Michelson | |
| 7,503,933 B2 | 3/2009 | Michelson | |
| 7,547,308 B2 | 6/2009 | Bertagnoli et al. | |
| 7,569,074 B2 | 8/2009 | Eisermann et al. | |
| 7,588,599 B2 | 9/2009 | Sweeney | |
| 7,618,458 B2 | 11/2009 | Biedermann et al. | |
| 7,621,951 B2 | 11/2009 | Glenn et al. | |
| 7,621,958 B2 | 11/2009 | Zdeblick et al. | |
| 7,655,043 B2 | 2/2010 | Peterman et al. | |
| 7,655,046 B2 | 2/2010 | Dryer et al. | |
| 7,678,148 B2 | 3/2010 | Peterman | |
| 7,703,727 B2 | 4/2010 | Selness | |
| 7,704,279 B2 | 4/2010 | Moskowitz et al. | |
| 7,708,778 B2 | 5/2010 | Gordon et al. | |
| 7,722,674 B1 | 5/2010 | Grotz | |
| 7,727,280 B2 | 6/2010 | McLuen | |
| 7,731,751 B2 | 6/2010 | Butler et al. | |
| 7,749,270 B2 | 7/2010 | Peterman | |
| 7,749,279 B2 | 7/2010 | Twomey et al. | |
| 7,753,958 B2 | 7/2010 | Gordon et al. | |
| 7,758,644 B2 | 7/2010 | Trieu | |
| 7,763,028 B2 | 7/2010 | Lim et al. | |
| 7,771,473 B2 | 8/2010 | Thramann | |
| 7,785,351 B2 | 8/2010 | Gordon et al. | |
| 7,789,914 B2 | 9/2010 | Michelson | |
| 7,794,480 B2 | 9/2010 | Gordon et al. | |
| 7,799,081 B2 | 9/2010 | McKinley | |
| 7,799,082 B2 | 9/2010 | Gordon et al. | |
| 7,819,921 B2 | 10/2010 | Grotz | |
| 7,824,445 B2 | 11/2010 | Biro et al. | |
| 7,828,848 B2 | 11/2010 | Chauvin et al. | |
| 7,828,849 B2 | 11/2010 | Lim | |
| 7,837,734 B2 | 11/2010 | Zucherman et al. | |
| 7,846,188 B2 | 12/2010 | Moskowitz et al. | |
| 7,846,206 B2 | 12/2010 | Oglaza et al. | |
| 7,850,733 B2 | 12/2010 | Baynham et al. | |
| 7,875,034 B2 | 1/2011 | Josse et al. | |
| 7,875,078 B2 | 1/2011 | Wysocki et al. | |
| 7,879,098 B1 | 2/2011 | Simmons, Jr. | |
| 7,909,869 B2 | 3/2011 | Gordon et al. | |
| 7,931,688 B2 | 4/2011 | Landry et al. | |
| 7,942,903 B2 | 5/2011 | Moskowitz et al. | |
| 7,951,180 B2 | 5/2011 | Moskowitz et al. | |
| 7,972,363 B2 | 7/2011 | Moskowitz et al. | |
| 7,985,258 B2 | 7/2011 | Zdeblick et al. | |
| 8,021,430 B2 | 9/2011 | Michelson | |
| 8,025,665 B2 | 9/2011 | Lim et al. | |
| 8,052,723 B2 | 11/2011 | Gordon et al. | |
| 8,062,375 B2 | 11/2011 | Glerum et al. | |
| 8,080,041 B2 | 12/2011 | Boehm, Jr. et al. | |
| 8,097,035 B2 | 1/2012 | Glenn et al. | |
| 8,105,358 B2 | 1/2012 | Phan | |
| 8,105,382 B2 | 1/2012 | Olmos et al. | |
| 8,118,870 B2 | 2/2012 | Gordon et al. | |
| 8,118,871 B2 | 2/2012 | Gordon et al. | |
| 8,123,810 B2 | 2/2012 | Gordon et al. | |
| 8,128,700 B2 | 3/2012 | Delurio et al. | |
| 8,147,550 B2 | 4/2012 | Gordon et al. | |
| 8,172,903 B2 | 5/2012 | Gordon et al. | |
| 8,187,332 B2 | 5/2012 | McLuen | |
| 8,216,314 B2 * | 7/2012 | Richelsoph | A61F 2/4425 623/17.15 |
| 8,221,501 B2 | 7/2012 | Eisermann et al. | |
| 8,221,502 B2 | 7/2012 | Branch, Jr. | |
| 8,241,331 B2 | 8/2012 | Arnin | |
| 8,257,370 B2 | 9/2012 | Moskowitz et al. | |
| 8,257,440 B2 | 9/2012 | Gordon et al. | |
| 8,262,666 B2 | 9/2012 | Baynham et al. | |
| 8,262,736 B2 | 9/2012 | Michelson | |
| 8,267,966 B2 | 9/2012 | McCormack et al. | |
| 8,273,129 B2 | 9/2012 | Baynham et al. | |
| 8,303,601 B2 | 11/2012 | Bandeira et al. | |
| 8,303,658 B2 | 11/2012 | Peterman | |
| 8,308,804 B2 | 11/2012 | Krueger | |
| 8,317,025 B1 | 11/2012 | Kolozs et al. | |
| 8,317,866 B2 | 11/2012 | Palmatier et al. | |
| 8,328,818 B1 | 12/2012 | Seifert et al. | |

(56) References Cited

U.S. PATENT DOCUMENTS

| | | | |
|---|---|---|---|
| 8,337,562 | B2 | 12/2012 | Landry et al. |
| 8,353,913 | B2 | 1/2013 | Moskowitz et al. |
| 8,361,152 | B2 | 1/2013 | McCormack et al. |
| 8,366,777 | B2 * | 2/2013 | Matthis ............... A61F 2/4425 623/17.11 |
| 8,377,071 | B2 | 2/2013 | Lim et al. |
| 8,382,842 | B2 | 2/2013 | Greenhalgh et al. |
| 8,398,713 | B2 | 3/2013 | Weiman |
| 8,403,990 | B2 | 3/2013 | Dryer et al. |
| 8,419,795 | B2 | 4/2013 | Sweeney |
| 8,425,558 | B2 | 4/2013 | McCormack et al. |
| 8,435,298 | B2 | 5/2013 | Weiman |
| 8,435,299 | B2 | 5/2013 | Chauvin et al. |
| 8,444,696 | B2 | 5/2013 | Michelson |
| 8,444,697 | B1 | 5/2013 | Butler et al. |
| 8,460,389 | B2 | 6/2013 | DeLurio et al. |
| 8,480,748 | B2 | 7/2013 | Poulos |
| 8,491,657 | B2 | 7/2013 | Attia et al. |
| 8,496,706 | B2 * | 7/2013 | Ragab .................. A61F 2/447 623/17.11 |
| 8,506,635 | B2 | 8/2013 | Palmatier et al. |
| 8,512,348 | B2 | 8/2013 | Chabansky et al. |
| 8,512,407 | B2 | 8/2013 | Butler et al. |
| 8,518,114 | B2 | 8/2013 | Marik |
| 8,518,120 | B2 | 8/2013 | Glerum et al. |
| 8,523,946 | B1 | 9/2013 | Swann |
| 8,545,567 | B1 | 10/2013 | Krueger |
| 8,556,975 | B2 | 10/2013 | Lechoslaw et al. |
| 8,556,979 | B2 | 10/2013 | Glerum et al. |
| 8,562,683 | B2 | 10/2013 | McKinley |
| 8,568,481 | B2 | 10/2013 | Olmos et al. |
| 8,574,300 | B2 | 11/2013 | McManus et al. |
| 8,579,907 | B2 | 11/2013 | Lim et al. |
| 8,579,980 | B2 | 11/2013 | DeLurio et al. |
| 8,579,981 | B2 | 11/2013 | Lim et al. |
| 8,597,360 | B2 | 12/2013 | McLuen et al. |
| 8,603,168 | B2 | 12/2013 | Gordon et al. |
| 8,623,054 | B2 | 1/2014 | McCormack et al. |
| 8,623,091 | B2 | 1/2014 | Suedkamp et al. |
| 8,628,578 | B2 * | 1/2014 | Miller .................. A61F 2/4425 623/17.16 |
| 8,641,767 | B2 | 2/2014 | Landry et al. |
| 8,641,769 | B2 | 2/2014 | Malandain |
| 8,647,386 | B2 | 2/2014 | Gordon et al. |
| 8,685,095 | B2 | 4/2014 | Miller et al. |
| 8,696,720 | B2 | 4/2014 | Lazarof |
| 8,702,798 | B2 | 4/2014 | Matthis et al. |
| 8,709,086 | B2 | 4/2014 | Glerum |
| 8,734,516 | B2 | 5/2014 | Moskowitz et al. |
| 8,747,444 | B2 | 6/2014 | Moskowitz et al. |
| 8,753,345 | B2 | 6/2014 | McCormack et al. |
| 8,753,347 | B2 | 6/2014 | McCormack et al. |
| 8,753,377 | B2 | 6/2014 | McCormack et al. |
| 8,753,398 | B2 | 6/2014 | Gordon et al. |
| 8,778,025 | B2 | 7/2014 | Ragab et al. |
| 8,784,450 | B2 | 7/2014 | Moskowitz et al. |
| 8,790,407 | B2 | 7/2014 | Chauvin et al. |
| 8,795,366 | B2 | 8/2014 | Varela |
| 8,828,062 | B2 | 9/2014 | McCormack et al. |
| 8,828,066 | B2 | 9/2014 | Lazarof |
| 8,834,472 | B2 | 9/2014 | McCormack et al. |
| 8,845,731 | B2 | 9/2014 | Weiman |
| 8,845,732 | B2 | 9/2014 | Weiman |
| 8,845,734 | B2 | 9/2014 | Weiman |
| 8,852,279 | B2 | 10/2014 | Weiman |
| 8,858,638 | B2 | 10/2014 | Michelson |
| 8,864,833 | B2 | 10/2014 | Glerum et al. |
| 8,870,959 | B2 | 10/2014 | Arnin |
| 8,888,853 | B2 | 11/2014 | Glerum et al. |
| 8,888,854 | B2 | 11/2014 | Glerum et al. |
| 8,894,652 | B2 | 11/2014 | Seifert et al. |
| 8,894,708 | B2 * | 11/2014 | Thalgott ................ A61B 17/86 623/17.11 |
| 8,894,711 | B2 | 11/2014 | Varela |
| 8,894,712 | B2 | 11/2014 | Varela |
| 8,906,099 | B2 | 12/2014 | Poulos |
| 8,920,507 | B2 | 12/2014 | Malandain |
| 8,926,701 | B2 | 1/2015 | De Lurio et al. |
| 8,926,704 | B2 | 1/2015 | Glerum et al. |
| 8,940,048 | B2 | 1/2015 | Butler et al. |
| 8,968,406 | B2 | 3/2015 | Arnin |
| 8,968,408 | B2 | 3/2015 | Schaller et al. |
| 8,974,534 | B2 | 3/2015 | Krueger |
| 8,986,389 | B2 | 3/2015 | Lim et al. |
| 8,992,621 | B2 | 3/2015 | Chauvin et al. |
| 8,998,992 | B2 | 4/2015 | Seifert et al. |
| 9,005,293 | B2 | 4/2015 | Moskowitz et al. |
| 9,011,492 | B2 | 4/2015 | McCormack et al. |
| 9,034,040 | B2 | 5/2015 | Seifert et al. |
| 9,034,041 | B2 | 5/2015 | Wolters et al. |
| 9,039,771 | B2 | 5/2015 | Glerum et al. |
| 9,055,985 | B2 | 6/2015 | Lazarof |
| 9,078,769 | B2 | 7/2015 | Farin |
| 9,095,446 | B2 | 8/2015 | Landry et al. |
| 9,101,488 | B2 | 8/2015 | Malandain |
| 9,119,730 | B2 | 9/2015 | Glerum et al. |
| 9,125,757 | B2 | 9/2015 | Weiman |
| 9,138,277 | B2 | 9/2015 | Fitzpatrick |
| 9,149,364 | B2 | 10/2015 | McManus et al. |
| 9,180,017 | B2 | 11/2015 | Poulos |
| 9,186,262 | B2 | 11/2015 | McLuen et al. |
| 9,192,484 | B2 | 11/2015 | Landry et al. |
| 9,204,974 | B2 | 12/2015 | Glerum et al. |
| 9,211,196 | B2 | 12/2015 | Glerum et al. |
| 9,216,095 | B2 | 12/2015 | Glerum et al. |
| 9,233,007 | B2 | 1/2016 | Sungarian et al. |
| 9,271,846 | B2 | 3/2016 | Lim et al. |
| 9,283,089 | B2 | 3/2016 | McKay |
| 9,301,854 | B2 | 4/2016 | Moskowitz et al. |
| 9,320,610 | B2 | 4/2016 | Alheidt et al. |
| 9,320,615 | B2 | 4/2016 | Suedkamp et al. |
| 9,351,848 | B2 | 5/2016 | Glerum et al. |
| 9,358,123 | B2 | 6/2016 | McLuen et al. |
| 9,358,126 | B2 | 6/2016 | Glerum et al. |
| 9,358,128 | B2 | 6/2016 | Glerum et al. |
| 9,358,129 | B2 | 6/2016 | Weiman |
| 9,398,961 | B2 | 7/2016 | Malandain |
| 9,408,707 | B2 | 8/2016 | Oglaza et al. |
| 9,408,708 | B2 | 8/2016 | Greenhalgh |
| 9,414,936 | B2 | 8/2016 | Miller et al. |
| 9,445,856 | B2 | 9/2016 | Seifert et al. |
| 9,445,919 | B2 | 9/2016 | Palmatier et al. |
| 9,452,063 | B2 | 9/2016 | Glerum et al. |
| 9,486,324 | B2 | 11/2016 | Hochschuler et al. |
| 9,492,287 | B2 | 11/2016 | Glerum et al. |
| 9,510,954 | B2 | 12/2016 | Glerum et al. |
| 9,510,955 | B2 | 12/2016 | Marino et al. |
| 9,526,627 | B2 | 12/2016 | Tabor et al. |
| 9,526,628 | B2 | 12/2016 | Krueger |
| 9,532,821 | B2 | 1/2017 | Moskowitz et al. |
| 9,539,108 | B2 | 1/2017 | Glerum et al. |
| 9,545,319 | B2 | 1/2017 | Farin |
| 9,549,824 | B2 | 1/2017 | McAfee |
| 9,566,168 | B2 | 2/2017 | Glerum et al. |
| 9,579,124 | B2 | 2/2017 | Gordon et al. |
| 9,579,215 | B2 | 2/2017 | Suedkamp et al. |
| 9,592,131 | B2 | 3/2017 | Sandstrom et al. |
| 9,597,200 | B2 | 3/2017 | Glerum et al. |
| 9,603,713 | B2 | 3/2017 | Moskowitz et al. |
| 9,622,791 | B2 | 4/2017 | McCormack et al. |
| 9,622,875 | B2 | 4/2017 | Moskowitz et al. |
| 9,629,665 | B2 | 4/2017 | McCormack et al. |
| 9,642,712 | B2 | 5/2017 | Schaller et al. |
| 9,655,747 | B2 | 5/2017 | Glerum et al. |
| 9,662,223 | B2 | 5/2017 | Matthis et al. |
| 9,675,385 | B2 | 6/2017 | Moskowitz et al. |
| 9,675,469 | B2 | 6/2017 | Landry et al. |
| 9,730,802 | B1 * | 8/2017 | Harvey ................ A61F 2/4455 |
| 9,801,734 | B1 * | 10/2017 | Stein .................... A61F 2/447 |
| 9,937,053 | B2 * | 4/2018 | Melkent .............. A61F 2/4455 |
| 9,962,272 | B1 * | 5/2018 | Daffinson ............ A61F 2/4611 |
| 2002/0040243 | A1 | 4/2002 | Attali et al. |
| 2002/0045945 | A1 | 4/2002 | Liu et al. |
| 2002/0161444 | A1 | 10/2002 | Choi |

(56) References Cited

U.S. PATENT DOCUMENTS

| | | |
|---|---|---|
| 2002/0165613 A1 | 11/2002 | Lin et al. |
| 2003/0135279 A1 | 7/2003 | Michelson |
| 2004/0087947 A1 | 5/2004 | Lim et al. |
| 2004/0133280 A1 | 7/2004 | Trieu |
| 2004/0254643 A1 | 12/2004 | Jackson |
| 2005/0107878 A1 | 5/2005 | Conchy |
| 2005/0171541 A1 | 8/2005 | Boehm, Jr. et al. |
| 2005/0192669 A1 | 9/2005 | Zdeblick et al. |
| 2005/0203625 A1 | 9/2005 | Boehm, Jr. et al. |
| 2005/0278036 A1 | 12/2005 | Leonard et al. |
| 2005/0283245 A1 | 12/2005 | Gordon et al. |
| 2006/0069436 A1 | 3/2006 | Sutton et al. |
| 2006/0095136 A1 | 5/2006 | McLuen |
| 2006/0122701 A1 | 6/2006 | Kiester |
| 2006/0195192 A1 | 8/2006 | Gordon et al. |
| 2006/0229729 A1 | 10/2006 | Gordon et al. |
| 2006/0241764 A1 | 10/2006 | Michelson |
| 2006/0241774 A1 | 10/2006 | Attali et al. |
| 2007/0050030 A1 | 3/2007 | Kim |
| 2007/0073406 A1 | 3/2007 | Gordon et al. |
| 2007/0270954 A1 | 11/2007 | Wu |
| 2007/0270963 A1* | 11/2007 | Melkent .................. A61F 2/442 623/17.11 |
| 2008/0021559 A1 | 1/2008 | Thramann |
| 2008/0051902 A1 | 2/2008 | Dwyer |
| 2008/0065219 A1* | 3/2008 | Dye ...................... A61F 2/4465 623/17.16 |
| 2008/0183204 A1 | 7/2008 | Greenhalgh et al. |
| 2009/0043394 A1 | 2/2009 | Zdeblick et al. |
| 2009/0198241 A1 | 8/2009 | Phan |
| 2009/0198245 A1 | 8/2009 | Phan |
| 2009/0198338 A1 | 8/2009 | Phan |
| 2009/0299478 A1 | 12/2009 | Carls et al. |
| 2010/0023057 A1 | 1/2010 | Aeschlimann et al. |
| 2010/0049325 A1 | 2/2010 | Biedermann et al. |
| 2010/0070041 A1 | 3/2010 | Peterman et al. |
| 2010/0152853 A1* | 6/2010 | Kirschman ............. A61F 2/447 623/17.11 |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234952 A1 | 9/2010 | Peterman |
| 2010/0241231 A1 | 9/2010 | Marino et al. |
| 2010/0249933 A1 | 9/2010 | Trieu |
| 2010/0286780 A1 | 11/2010 | Dryer et al. |
| 2011/0015742 A1 | 1/2011 | Hong |
| 2011/0029086 A1 | 2/2011 | Glazer et al. |
| 2011/0137349 A1 | 6/2011 | Moskowitz et al. |
| 2011/0208312 A1 | 8/2011 | Moskowitz et al. |
| 2011/0218627 A1 | 9/2011 | Rampersaud et al. |
| 2011/0238184 A1 | 9/2011 | Zdeblick et al. |
| 2012/0058451 A1 | 3/2012 | Lazarof |
| 2012/0059472 A1 | 3/2012 | Weiman |
| 2012/0059481 A1 | 3/2012 | Abernathie et al. |
| 2012/0109319 A1 | 5/2012 | Perisic |
| 2012/0197405 A1 | 8/2012 | Cuevas et al. |
| 2012/0245691 A1 | 9/2012 | Reimels |
| 2012/0277861 A1 | 11/2012 | Steele et al. |
| 2012/0330419 A1 | 12/2012 | Moskowitz et al. |
| 2012/0330421 A1 | 12/2012 | Weiman |
| 2013/0013070 A1 | 1/2013 | McCormack et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0053962 A1 | 2/2013 | Moskowitz et al. |
| 2013/0103153 A1 | 4/2013 | Blackwell et al. |
| 2013/0103154 A1 | 4/2013 | Trieu et al. |
| 2013/0110168 A1 | 5/2013 | McCormack et al. |
| 2013/0110248 A1 | 5/2013 | Zipnick |
| 2013/0116791 A1 | 5/2013 | Theofilos |
| 2013/0144388 A1 | 6/2013 | Emery et al. |
| 2013/0178940 A1 | 7/2013 | Farley |
| 2013/0204371 A1 | 8/2013 | McLuen et al. |
| 2013/0231747 A1 | 9/2013 | Olmos et al. |
| 2013/0297028 A1 | 11/2013 | Zipnick |
| 2013/0297029 A1 | 11/2013 | Kana et al. |
| 2013/0310935 A1 | 11/2013 | Swann |
| 2014/0107790 A1 | 4/2014 | Combrowski |
| 2014/0249629 A1 | 9/2014 | Moskowitz et al. |
| 2014/0296916 A1 | 10/2014 | McCormack et al. |
| 2015/0081021 A1 | 3/2015 | Ciupik |
| 2015/0094814 A1 | 4/2015 | Emerick et al. |
| 2015/0105824 A1 | 4/2015 | Moskowitz et al. |
| 2015/0216518 A1 | 8/2015 | McCormack et al. |
| 2015/0230931 A1 | 8/2015 | Greenhalgh |
| 2015/0230934 A1 | 8/2015 | Chauvin et al. |
| 2015/0374507 A1 | 12/2015 | Wolters et al. |
| 2016/0008040 A1 | 1/2016 | McCormack et al. |
| 2016/0015527 A1 | 1/2016 | McManus et al. |
| 2016/0015529 A1 | 1/2016 | Reimels |
| 2016/0030191 A1 | 2/2016 | McLuen et al. |
| 2016/0058579 A1 | 3/2016 | Aeschlimann et al. |
| 2016/0135961 A1 | 5/2016 | Aeschlimann et al. |
| 2016/0143748 A1 | 5/2016 | Lim et al. |
| 2016/0193056 A1 | 7/2016 | McKay |
| 2016/0213482 A1 | 7/2016 | Alheidt et al. |
| 2016/0242932 A1 | 8/2016 | McLuen et al. |
| 2016/0296340 A1 | 10/2016 | Gordon et al. |
| 2016/0302943 A1 | 10/2016 | Oglaza et al. |
| 2016/0310291 A1 | 10/2016 | Greenhalgh |
| 2016/0317315 A1 | 11/2016 | Weiman |
| 2016/0324659 A1 | 11/2016 | Malandain |
| 2016/0324661 A1 | 11/2016 | Miller et al. |
| 2016/0354131 A1 | 12/2016 | Seifert et al. |
| 2016/0374826 A1 | 12/2016 | Palmatier et al. |
| 2016/0374830 A1 | 12/2016 | Moskowitz et al. |
| 2017/0035468 A1 | 2/2017 | McCormack et al. |
| 2017/0035576 A1 | 2/2017 | Schaller et al. |
| 2017/0086986 A1 | 3/2017 | McAfee |
| 2017/0100255 A1* | 4/2017 | Hleihil .................. A61F 2/447 |
| 2017/0119539 A1 | 5/2017 | Glerum et al. |
| 2017/0119540 A1 | 5/2017 | Greenhalgh |
| 2017/0119541 A1 | 5/2017 | Greenhalgh |
| 2017/0119542 A1 | 5/2017 | Logan et al. |
| 2017/0119546 A1 | 5/2017 | Farin |
| 2017/0128229 A1 | 5/2017 | Suedkamp et al. |
| 2017/0165083 A1 | 6/2017 | Greenhalgh |

FOREIGN PATENT DOCUMENTS

| | | |
|---|---|---|
| AU | 2011203582 | 8/2011 |
| CA | 1337842 | 1/1996 |
| CA | 2447257 | 12/1996 |
| CN | 2668075 | 1/2005 |
| CN | 1621015 | 6/2005 |
| CN | 2730336 | 10/2005 |
| CN | 201861800 | 4/2006 |
| CN | 101268963 | 9/2008 |
| CN | 202191381 | 4/2012 |
| CN | 202235781 | 5/2012 |
| CN | 203001182 | 6/2013 |
| CN | 103356310 | 10/2013 |
| DE | 4012622 | 7/1991 |
| DE | 4416605 | 6/1995 |
| DE | 10241948 | 4/2004 |
| DE | 102005033608 | 1/2007 |
| DE | 102010004133 | 9/2011 |
| DE | 102012203256 | 9/2013 |
| EP | 0635246 | 1/1995 |
| EP | 0880950 | 12/1998 |
| EP | 1290985 | 3/2003 |
| EP | 1382315 | 1/2004 |
| EP | 1532949 | 5/2005 |
| EP | 1541096 | 6/2005 |
| EP | 1889587 | 2/2008 |
| EP | 2213263 | 8/2010 |
| EP | 2226039 | 9/2010 |
| EP | 2510904 | 10/2012 |
| ES | 2067421 | 3/1995 |
| ES | 2099008 | 5/1997 |
| FR | 2707477 | 1/1995 |
| FR | 2708192 | 2/1995 |
| FR | 2717068 | 9/1995 |

(56) References Cited

FOREIGN PATENT DOCUMENTS

| | | |
|---|---|---|
| FR | 2803741 | 7/2001 |
| FR | 2815845 | 5/2002 |
| FR | 2866228 | 8/2005 |
| FR | 2866229 | 8/2005 |
| FR | 2874814 | 3/2006 |
| FR | 2943529 | 10/2010 |
| FR | 2943530 | 10/2010 |
| FR | 2981261 | 4/2013 |
| JP | 2005137418 | 6/2005 |
| JP | 2008054710 | 3/2008 |
| JP | 2008126085 | 6/2008 |
| KR | 20010112139 | 12/2001 |
| KR | 20020025647 | 4/2002 |
| KR | 100410823 | 1/2003 |
| KR | 20030012142 | 2/2003 |
| KR | 20040064577 | 7/2004 |
| KR | 20050064501 | 6/2005 |
| KR | 20080001064 | 1/2008 |
| KR | 20080042341 | 5/2008 |
| KR | 100953930 | 4/2010 |
| KR | 20120119812 | 10/2012 |
| KR | 20130082281 | 7/2013 |
| RU | 2063730 | 7/1996 |
| RU | 2210343 | 8/2003 |
| RU | 105157 | 6/2011 |
| RU | 2460499 | 9/2012 |
| RU | 131611 | 8/2013 |
| SU | 988281 | 1/1983 |
| SU | 1424826 | 9/1988 |
| WO | WO9000037 | 1/1990 |
| WO | WO9531158 | 11/1995 |
| WO | WO9700054 | 1/1997 |
| WO | WO9926562 | 6/1999 |
| WO | WO200074605 | 12/2000 |
| WO | WO200392507 | 11/2003 |
| WO | WO2004012634 | 2/2004 |
| WO | WO2006081843 | 8/2006 |
| WO | WO2006117463 | 11/2006 |
| WO | WO2006134262 | 12/2006 |
| WO | WO2007009107 | 1/2007 |
| WO | WO2007028706 | 3/2007 |
| WO | WO2008132322 | 11/2008 |
| WO | WO2009064787 | 5/2009 |
| WO | WO2010148112 | 12/2010 |
| WO | WO2011142761 | 11/2011 |
| WO | WO2012031267 | 3/2012 |
| WO | WO2013152257 | 10/2013 |

* cited by examiner

LORDOTIC EXPANDABLE INTERBODY IMPLANT

CROSS REFERENCE TO RELATED APPLICATIONS

This application is a continuation of U.S. patent application Ser. No. 14/456,640, filed Aug. 11, 2014 (now U.S. Pat. No. 9,801,734), which claims the benefit of the filing date of U.S. Provisional Application No. 61/864,132, which was filed on Aug. 9, 2013. The contents of U.S. application Ser. No. 61/864,132 are incorporated by reference in their entirety as part of this application.

BACKGROUND

This application relates to expandable interbody spinal fusion implants and methods of use thereof.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary sill in the art having the benefit of this disclosure. The expandable spinal fusion implant and related methods disclosed herein boasts a variety of inventive features and components that warrant patent protection, both individually and in combination.

In general, the expandable spinal fusion implants described in this document include a housing, upper and lower endplates, a translating wedge positioned between the upper and lower endplates and within the housing, and a drive mechanism to drive translation of the wedge. The expandable spinal fusion implant is designed to be inserted into the disc space between adjacent vertebral bodies from a posterior approach. The implant may be made of any suitable, biocompatible material or combination of materials. For example, the implant components may be metal, poly ether ether ketone (PEEK), or a combination of the metal and PEEK. The implant is configured to be inserted into the disc space in a collapsed state and upon being seated in a desired location within the disc space the distal end of the implant is expanded in height to create an implant with a lordotic angle (i.e. the anterior height of the implant is greater than the posterior height of the implant, thereby restoring a more natural lordotic curvature of the particular segment of the lumbar spine). The expansion is accomplished by engaging the drive mechanism with a tool to activate the drive mechanism and cause the translating wedge to move between the implants in a distal direction.

Figure 1:
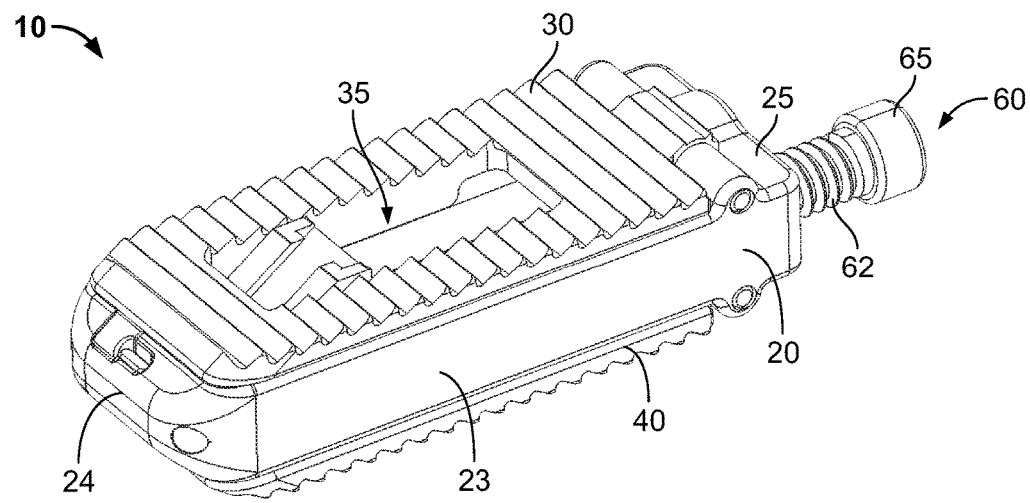
FIG. 1 is a perspective view of an expandable spinal fusion implant in a collapsed position, according to an exemplary embodiment.
Figure 2:
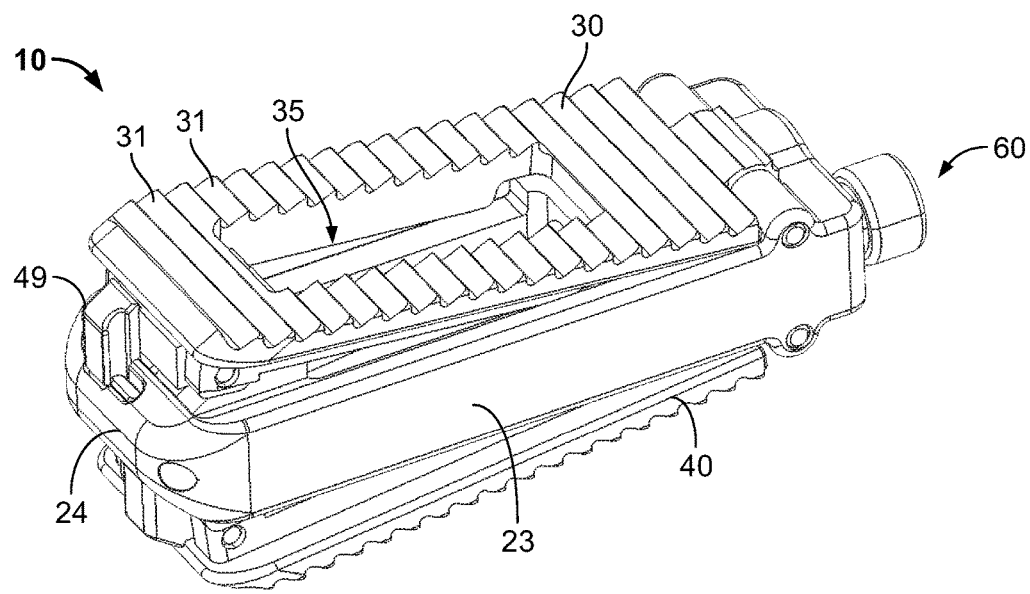
FIG. 2 is a perspective view of the expandable spinal fusion implant of FIG. 1 in an expanded position.
Figure 3:
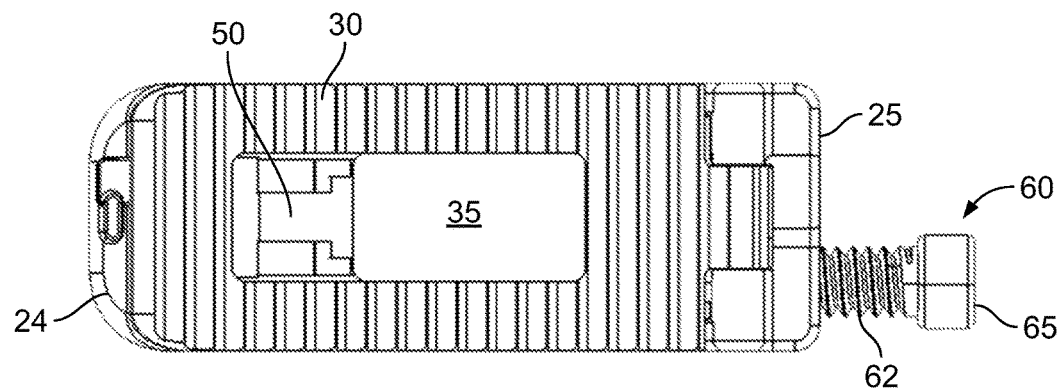
FIG. 3 is a top view of the expandable spinal fusion implant of FIG. 1.
Figure 4:
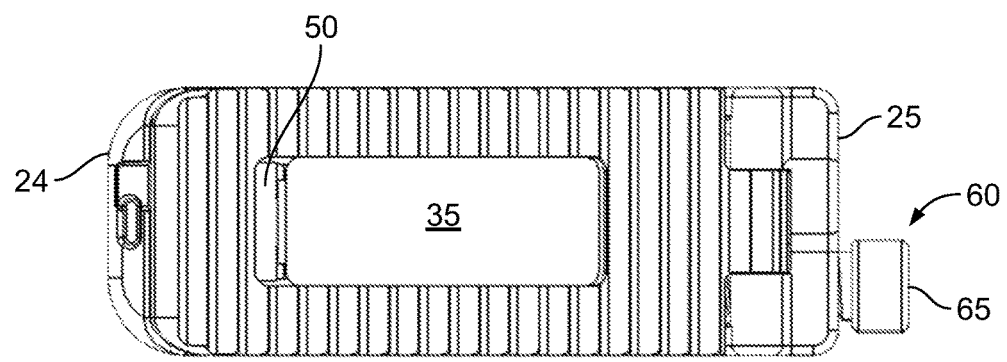
FIG. 4 is a top view of the expandable spinal fusion implant of FIG. 2.
Figure 5:
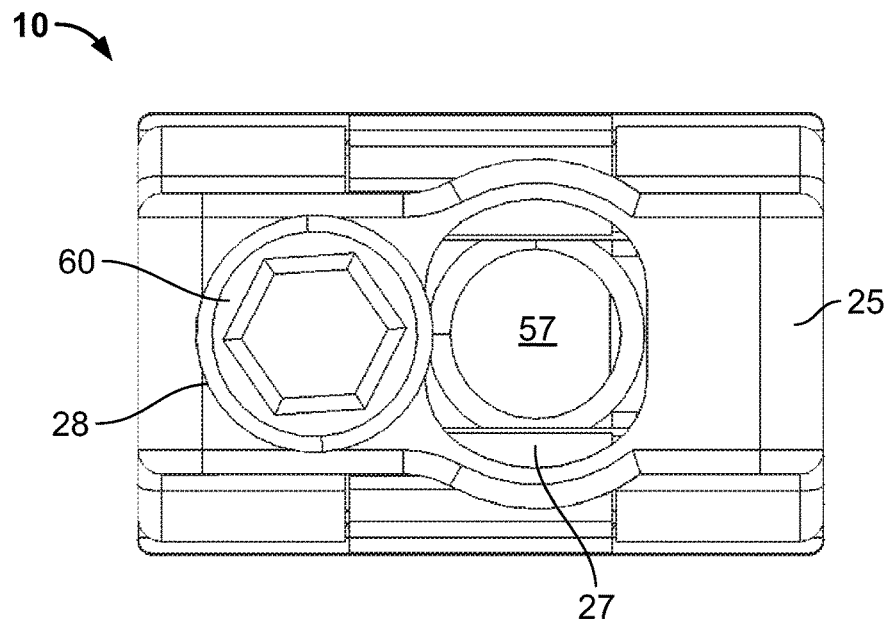
FIG. 5 is a back view of the expandable spinal fusion implant of FIG. 1.
Figure 6:
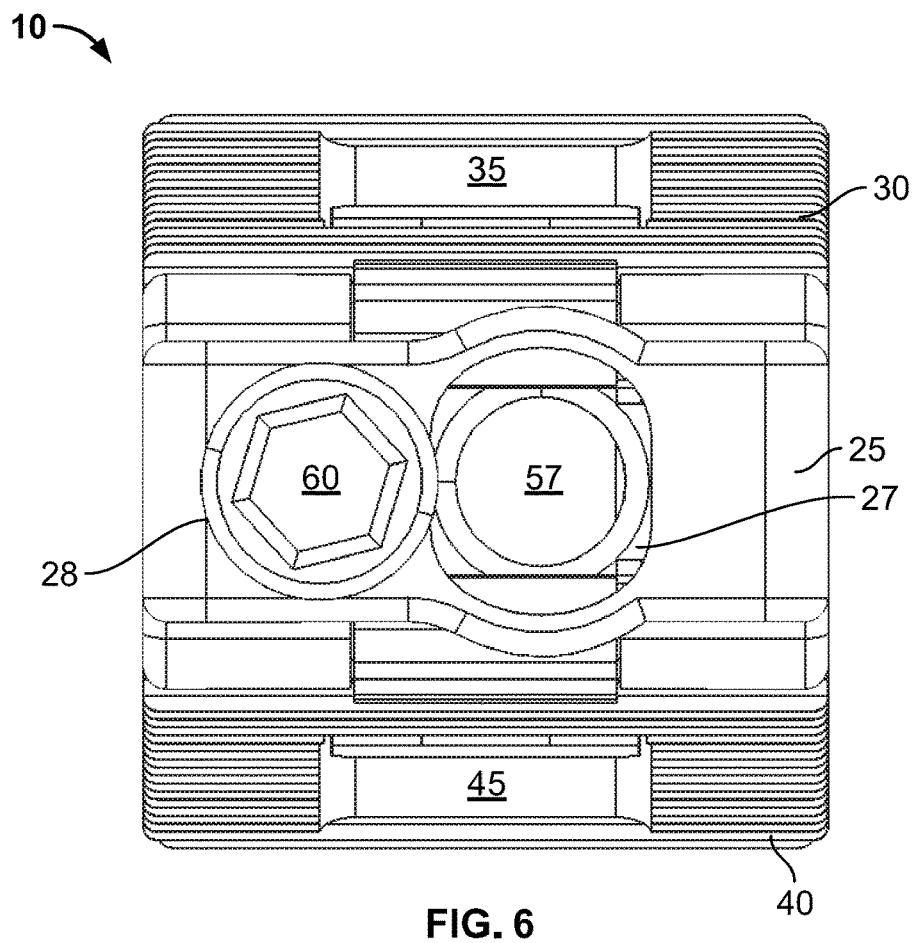
FIG. 6 is a back view of the expandable spinal fusion implant of FIG. 2.
Figure 7:
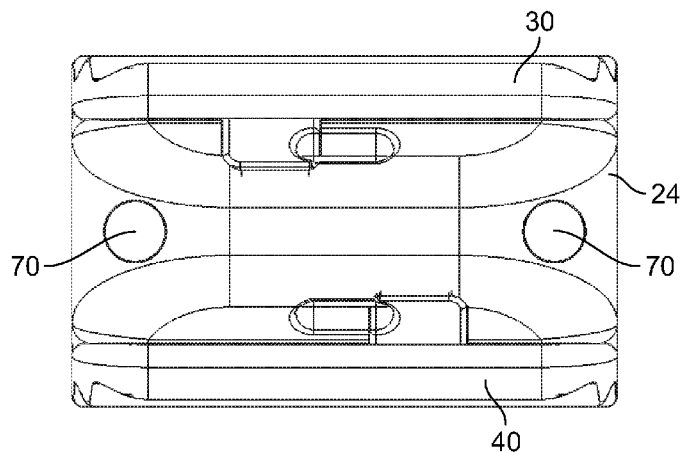
FIG. 7 is a front view of the expandable spinal fusion implant of FIG. 1.
Figure 8:
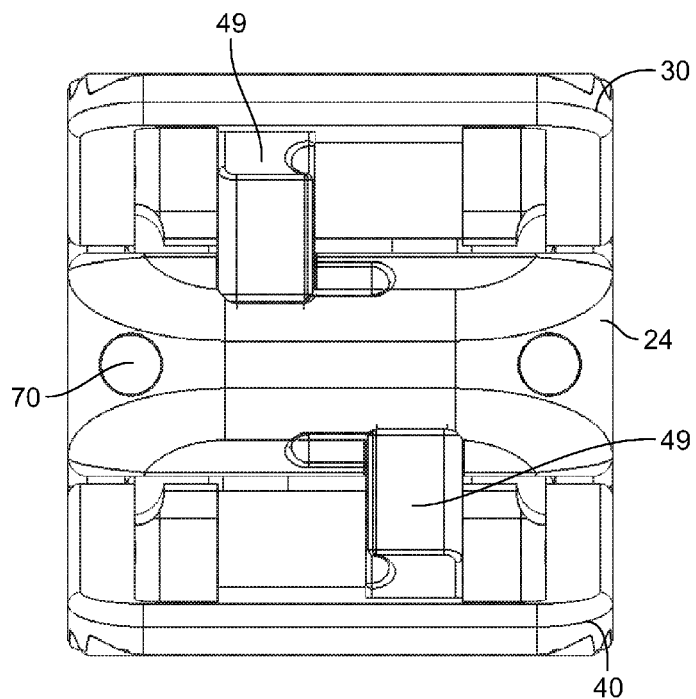
FIG. 8 is a front view of the expandable spinal fusion implant of FIG. 2.
Figure 9:
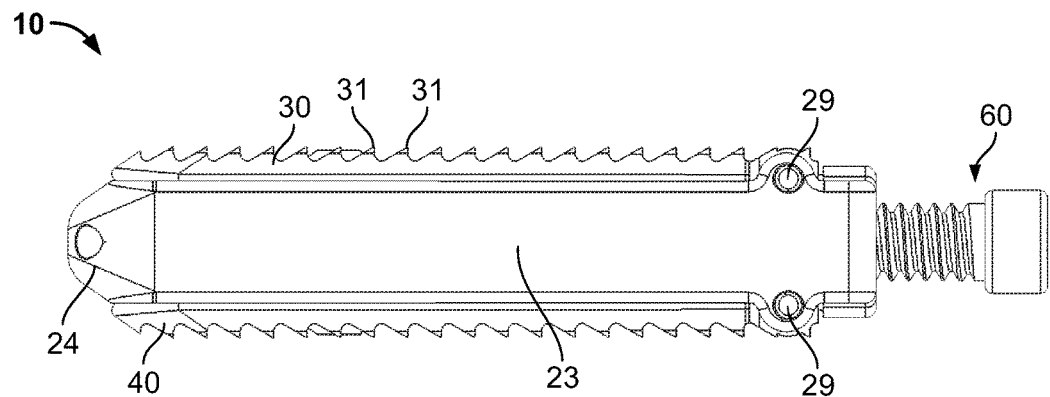
FIG. 9 is a side view of the expandable spinal fusion implant of FIG. 1.
Figure 10:
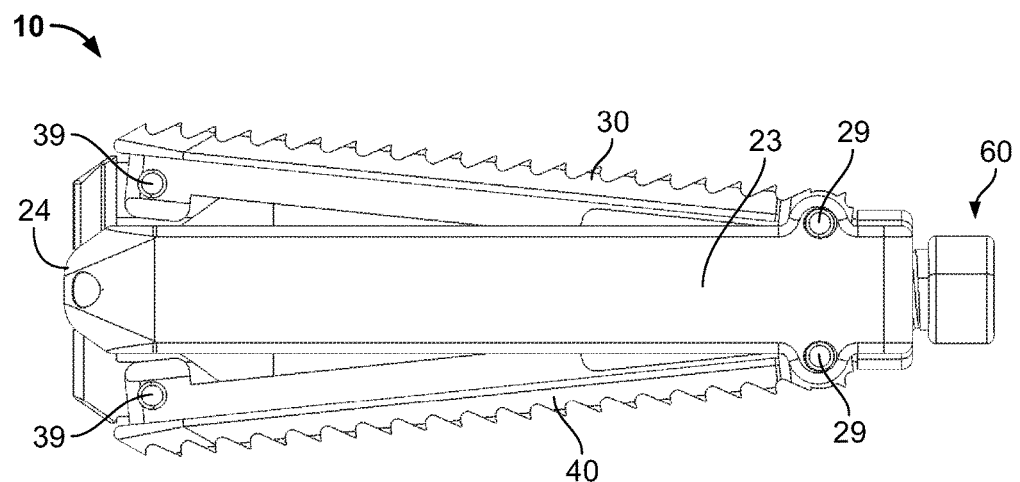
FIG. 10 is a side view of the expandable spinal fusion implant of FIG. 2.
Figure 11:
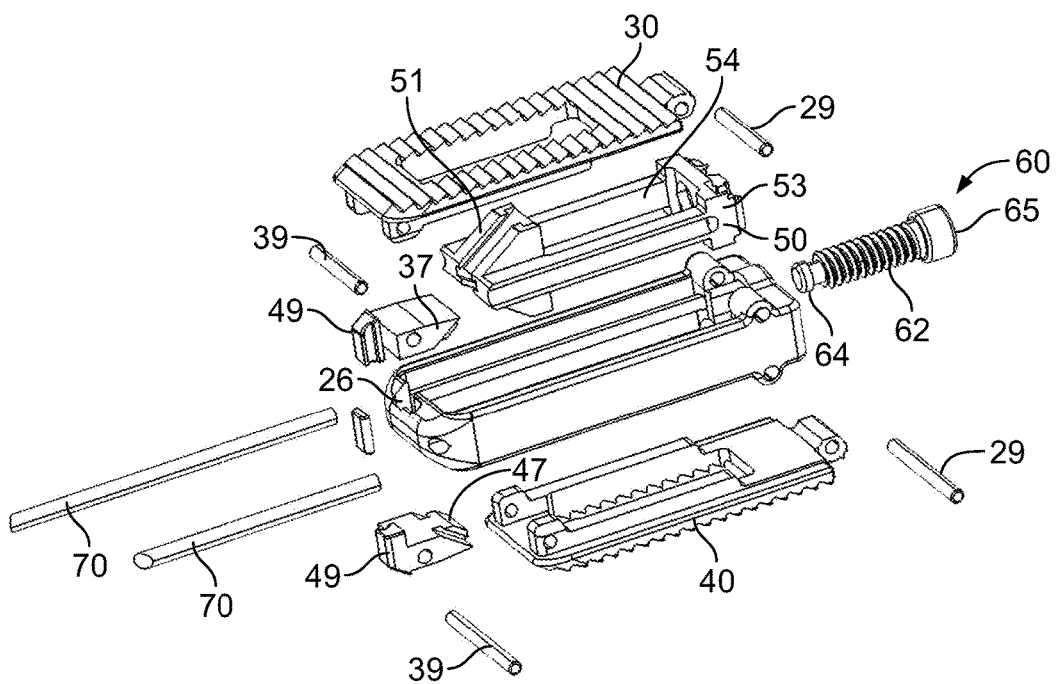
FIG. 11 is an exploded perspective view of the expandable spinal fusion implant of FIG. 1.

FIGS. 1-15 illustrate an exemplary embodiment of the expandable spinal fusion implant 10. The implant 10 includes a housing 20. The housing 20 is comprised of first and second lateral walls 22, 23, a distal or leading end wall 24 and a proximal or trailing end wall 25. The lateral walls 22, 23 and distal 24 and proximal 25 walls define a hollow interior of the housing 20. According to this embodiment, the first and second lateral walls 22, 23 are of equal length and the length of the lateral walls 22, 23 spans the length of the implant 10. The distal wall 24 is tapered, increasing in height from the distal most point to the point where it meets the lateral walls 22, 23 to aid in insertion of the implant 10 into the disc space. As illustrated in the exemplary embodiment, the distal wall 24 may also include a slots 26 dimensioned to receive complementary projections 49 extending from the upper and lower endplates 30, 40. The slots comprise a first slot in the upper surface of the distal end 24 of the housing 20 for receiving a projection from the upper endplate 30 and a second slot in the lower surface of the distal end 24 of the housing 20 for receiving a projection 49 from the lower endplate 40. The proximal wall 25 of the housing is best illustrated in FIGS. 5 and 6. The proximal wall 25 includes two apertures. The first is a graft delivery port 27 and the second is a drive screw aperture 28. The drive screw aperture 28 is offset from the mid longitudinal axis of the implant 10 to facilitate packing of graft into the hollow interior of the housing 10 through the graft delivery port 27 upon implantation of the implant 10 into the disc space. The housing 20 has a static height that remains unchanged when the implant 10 is in its collapsed configuration and in its expanded configuration. The maximum height of the housing 20 is less than the maximum height of the overall implant 10.

According to the embodiment of FIGS. 1-15, the housing 20 is coupled to the upper and lower endplates 30, 40 via pins 29 adjacent the proximal end 15 of the implant 10. The upper and lower endplates 30, 40 have identical features as described below. Each endplate 30, 40 has a bone contacting surface 32, 42 and an interior surface 34, 44. The endplates 30, 40 have a width that is equal to the width of the overall implant and equal to the width of the housing 20. The perimeter of the interior surfaces 34, 44 of the endplates 30, 40 rests adjacent the lateral walls 22, 23 of the housing 20 when the implant 10 is in its collapsed configuration. The upper and lower endplates 30, 40 according to this embodiment are generally rectangular and include a central fusion aperture 35, 45. The central fusion apertures 35, 45 are in communication with the hollow interior of the housing 20 and the central fusion aperture 55 of the wedge 50 to allow for bone growth through the implant 10 after the implant 10 has been place within the disc space of a patient. The endplates further include anti-migration features 31, 41 on their respective bone contacting surfaces 32, 42. The interior surface 34, 44 of each endplate 30, 40 includes an extension 36, 46 coupled to the endplate 30, 40 via a pin 39. The extensions 36, 46 include a projection 39 at the distal end and a ramp 37, 47 at the proximal end. The ramps 37, 47 engage the superior and inferior angled surfaces 51, 52 on the wedge 50 to allow for expansion of the height of the implant 10 as the wedge 50 is driven distally within the implant 10. As illustrated in the exemplary embodiment of FIGS. 1-15, the ramps 37, 47 and angled surfaces 51, 52 of the wedge may include mating features to couple the wedge 50 to the endplates 30, 40. In the exemplary embodiment, this mating feature is a dovetail connection, though other mating features may be employed in the alternative.

As illustrated by the exemplary embodiment of FIGS. 1-15, the implant 10 includes a wedge 50 housed between the upper and lower endplates 30, 40 and within the hollow interior of the housing 20. The wedge 50 includes first and second opposing angled surfaces 51, 52 at its distal end and a drive block 53 at its proximal end. The opposing angled surfaces 51, 52 and drive block 53 are connected via a pair of lateral arms 54 extending therebetween. The opposing angled surfaces 51, 52, lateral arms 54 and drive block 53 reside inside the hollow interior of the housing 20 and define a central aperture 55 that is in communication with the central apertures 35, 45 of the upper and lower endplates 30, 40. Optionally, the lateral arms 54 of the wedge 50 may engage rails 70 that rest in between a recess in the exterior surface of the lateral arms 54 and the interior surface of the lateral walls 22, 23 of the housing 20. The drive block 53 includes a graft aperture 57 extending through its thickness. The graft aperture 57 of the drive block 53 is in communication with the graft delivery port 27 in the proximal wall 25 of the housing 20 to allow graft material to be pass through the housing 20 and wedge 50 into the interior of the implant 10. The drive block 53 also includes a receptacle 56 dimensioned to house the distal end 64 of the drive mechanism 60.

According to the exemplary embodiment of FIGS. 1-15, the drive mechanism 60 is a screw. The drive screw 60 has a proximal end 64 and a distal end 65 and a threaded shaft 62 extending between the proximal end 64 and the distal end 65. The proximal end 64 includes a mating feature 63 for engaging a driving tool (not shown). The distal end 65 is configured to complement the shape of the receptacle 56 of the drive block 53. The threaded shaft of 62 of the drive screw is configured to be received in a complementary threaded drive screw aperture 28 in the housing 20, such that as the drive screw 60 is rotated, it translates distally through the drive screw aperture 28 and consequently pushes the wedge 50 distally. When the wedge 50 is urged distally, the opposing angled surfaces 51, 52 engage the ramps 37, 47 on the endplates 30, 40 thereby increasing the distance between the distal ends of the endplates 30, 40 and increasing the distal height of the implant 10.

Figure 12:
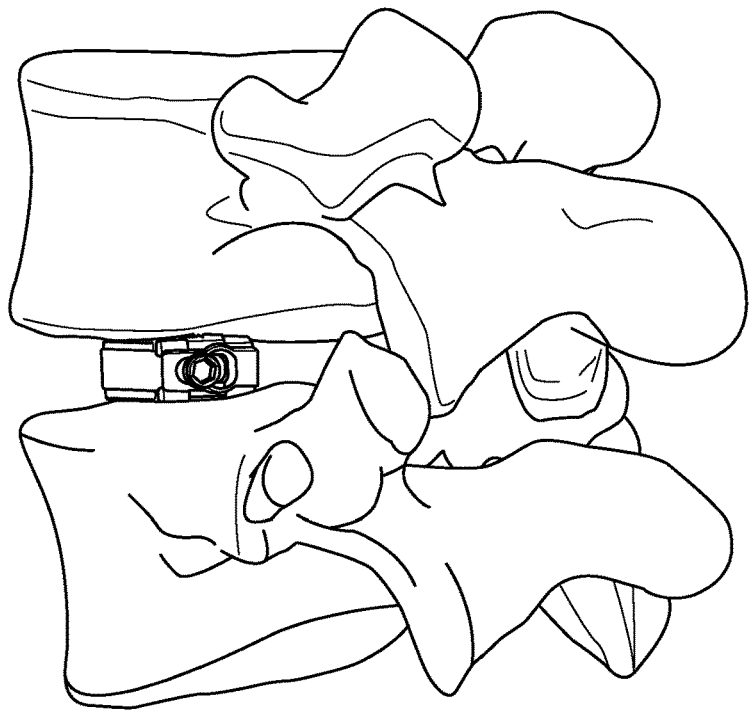
FIG. 12 is a perspective view of the expandable spinal fusion implant of FIG. implanted into the intervertebral space of a spine.
Figure 13:
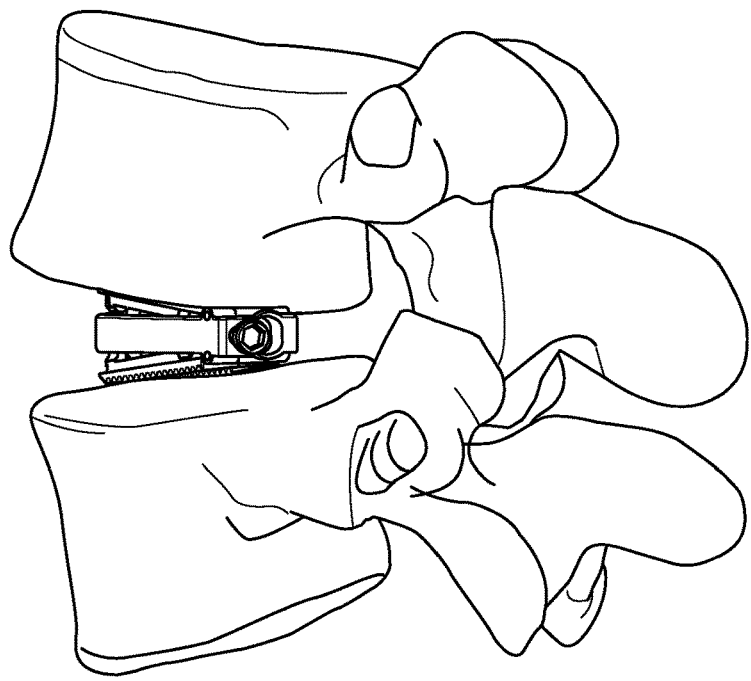
FIG. 13 is a perspective view of the expandable spinal fusion implant of FIG. 12 in its expanded configuration.
Figure 14:
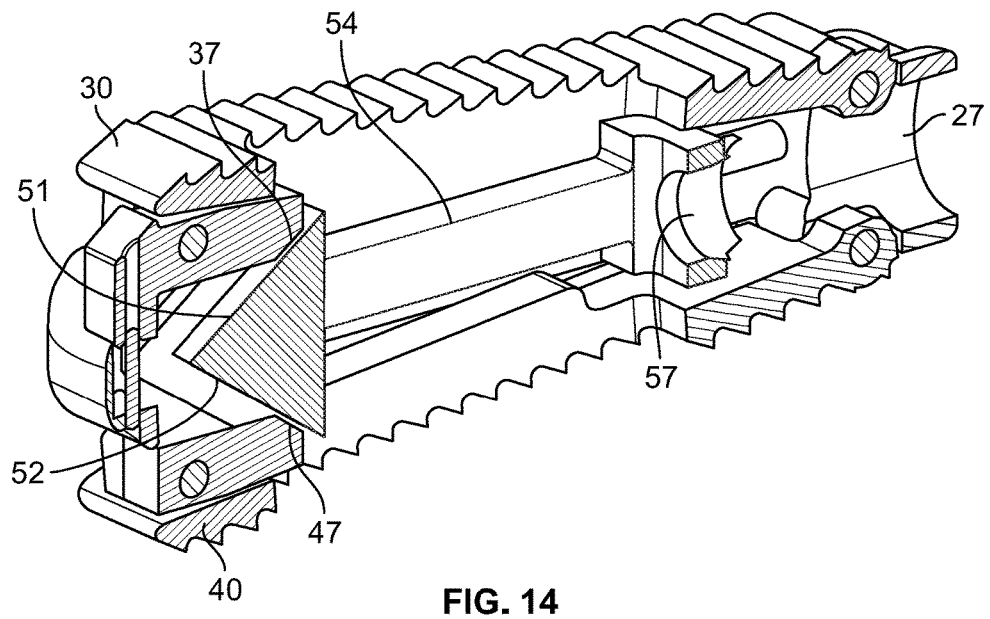
FIG. 14 is a perspective cross-sectional view of the expandable spinal fusion implant of FIG. 2.
Figure 15:
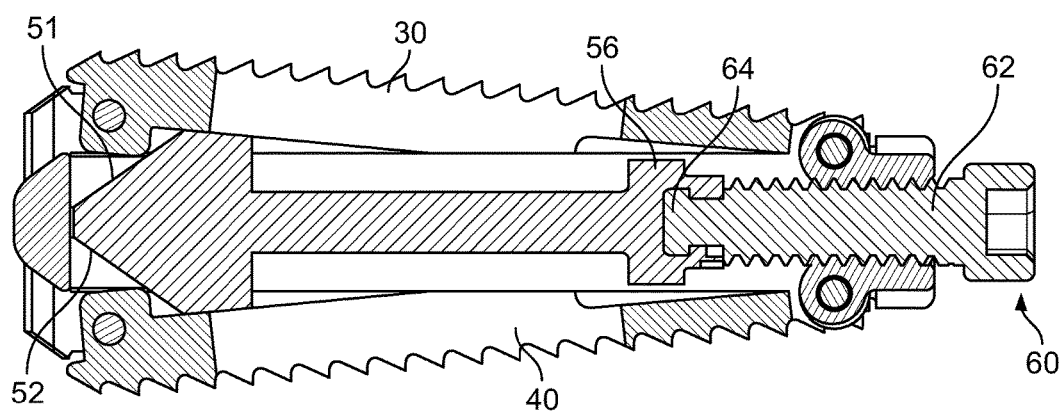
FIG. 15 is a side cross-sectional view of the expandable spinal fusion implant of FIG. 2.
Figure 16:
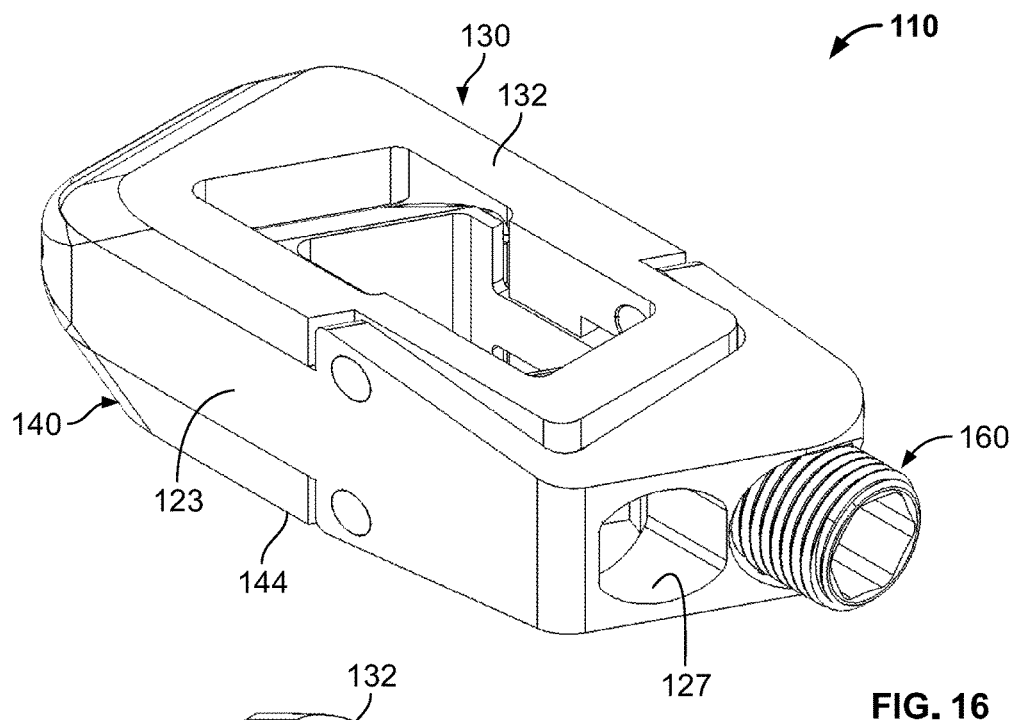
FIG. 16 is a perspective view of an expandable spinal fusion implant in a collapsed position according to an alternative embodiment.
Figure 17:
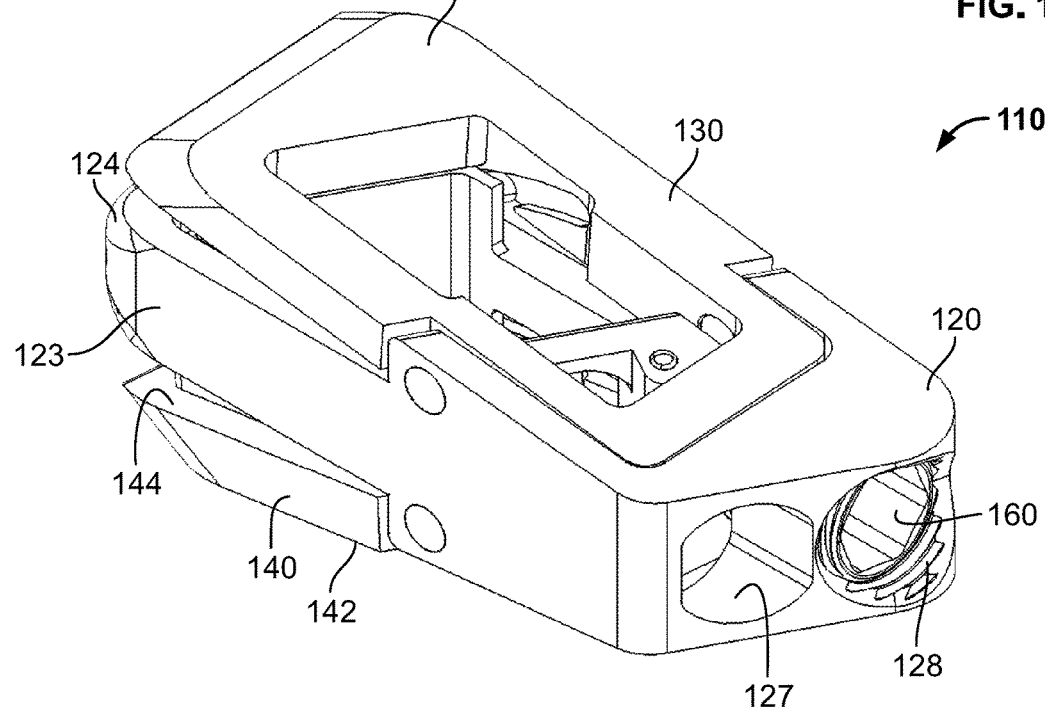
FIG. 17 is a perspective view of an expandable spinal fusion implant in an expanded configuration according to the alternative embodiment of FIG. 16.
Figure 18:
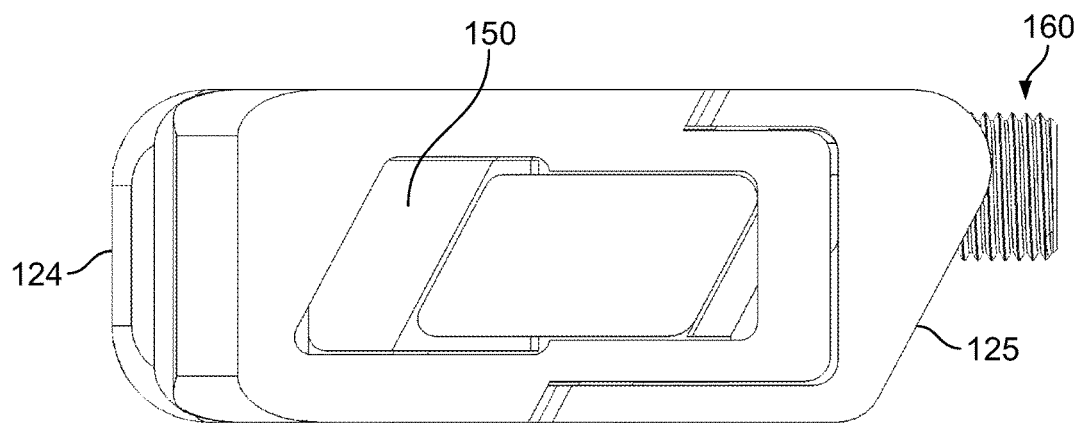
FIG. 18 is top view of the expandable spinal fusion implant of FIG. 16.
Figure 19:
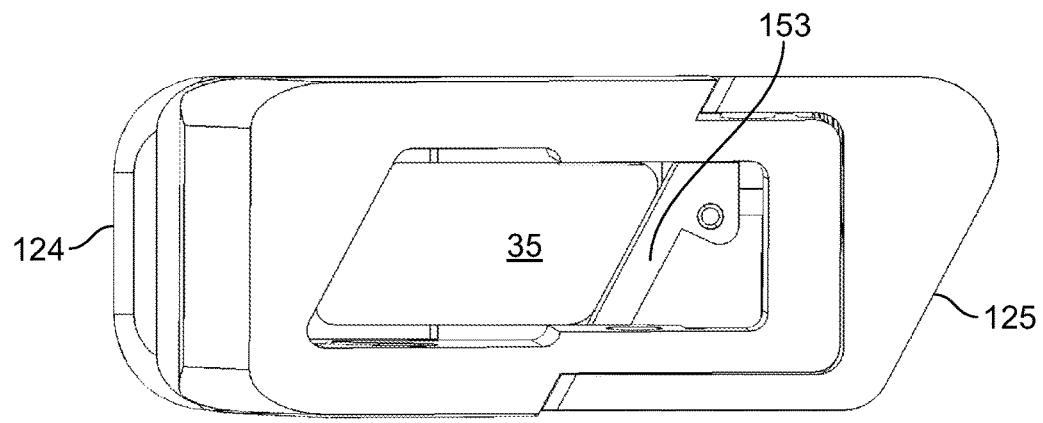
FIG. 19 is a top view of the expandable spinal fusion implant of FIG. 17.
Figure 20:
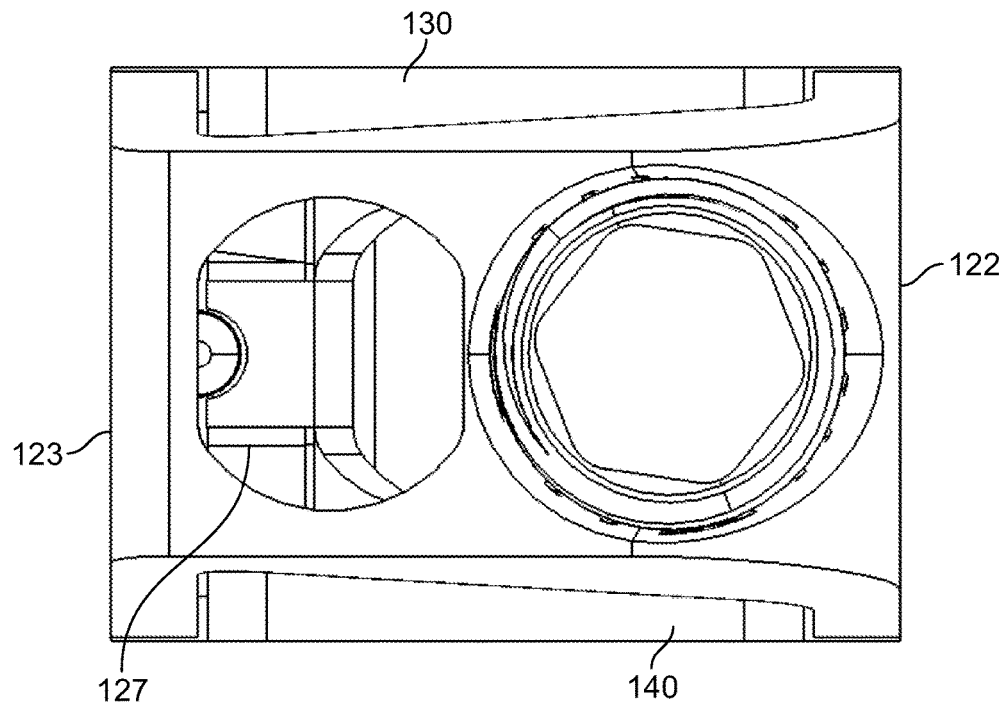
FIG. 20 is a back view of the expandable spinal fusion implant of FIG. 16.
Figure 21:
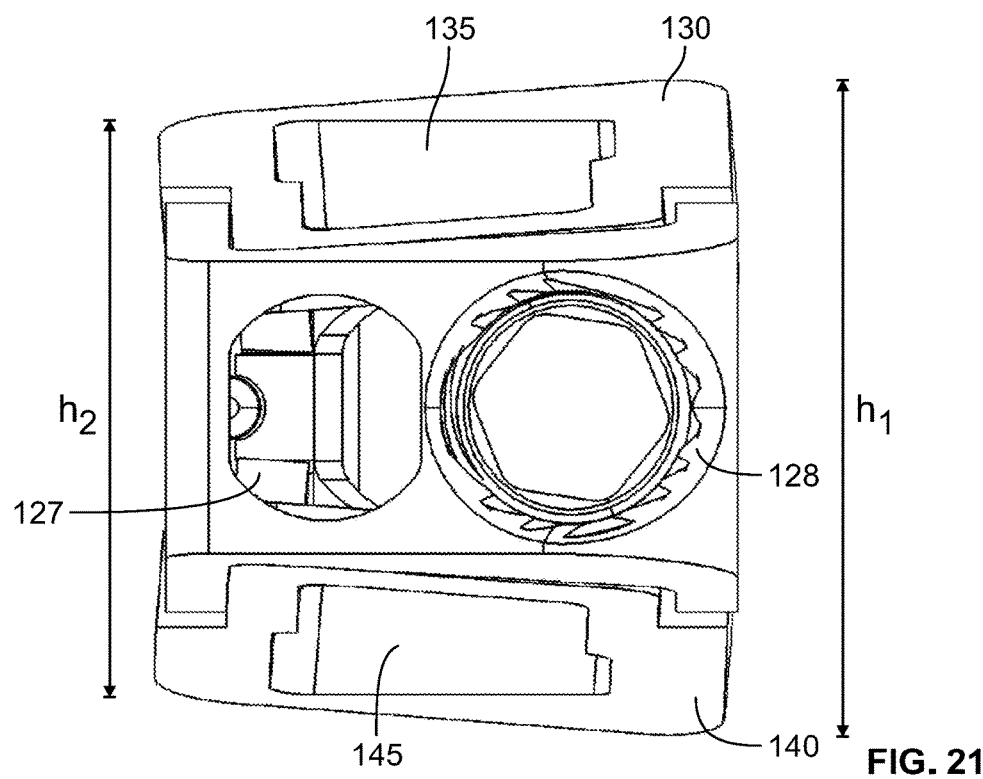
FIG. 21 is a back view of the expandable spinal fusion implant of FIG. 17.
Figure 22:
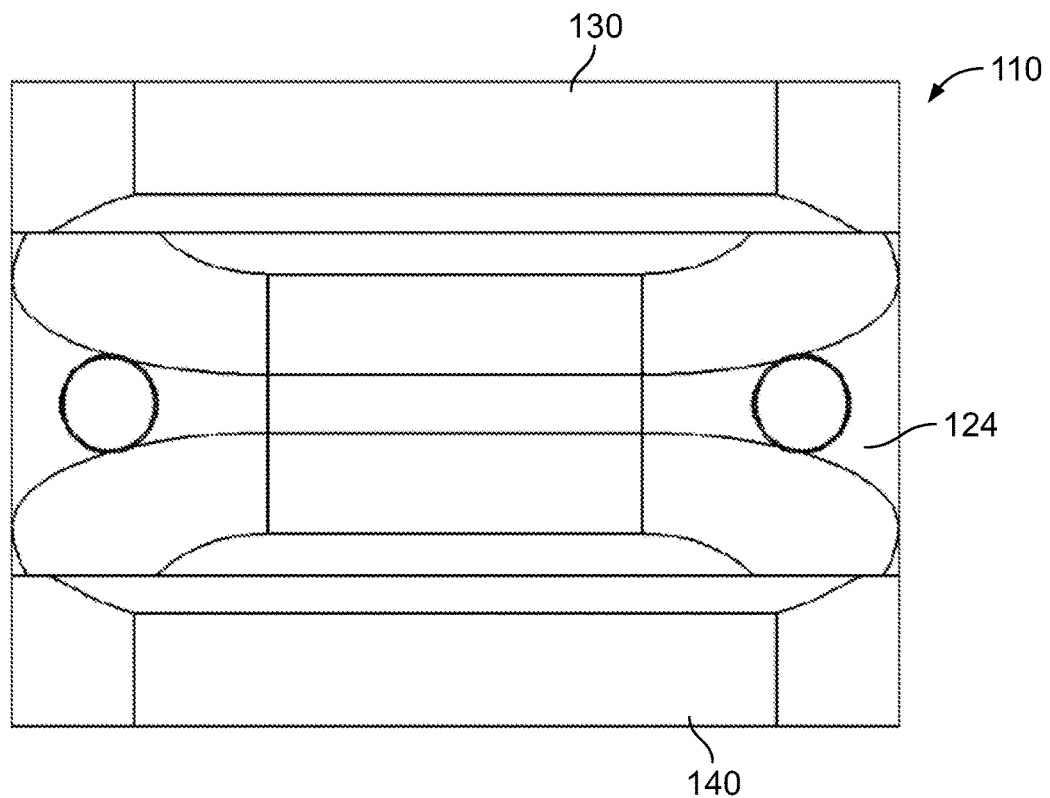
FIG. 22 is a front view of the expandable spinal fusion implant of FIG. 16.

In use according to this exemplary embodiment, the implant 10 implant is inserted into the disc space between adjacent vertebral bodies in its collapsed position as illustrated in FIG. 12. The collapsed configuration of the implant is illustrated in FIGS. 1, 3, 5, 7 and 9. Once the implant 10 has been placed in the desired position within the disc space, the drive screw 60 is engaged with a driving tool and rotated to advance the drive screw 60 distally within the implant, thereby advancing the wedge 50 distally and causing the upper and lower endplates 30, 40 to separate at the distal end 14 of the implant 10. When the drive screw has been fully advanced, the implant 10 is in its fully expanded configuration as illustrated in FIG. 13. Upon desired expansion of the implant, graft material is inserted into the interior of the implant through the graft delivery port 27 and graft aperture 57 of the wedge in the proximal end of the implant.

FIGS. 16-27 illustrate an alternative embodiment of the expandable spinal fusion implant 110. The implant 110 according to this alternative embodiment has many of the same features as described for the implant 10 in FIGS. 1-15 which are not necessarily repeated in detail here. The implant 110 according to the alternative embodiment shown in FIGS. 16-27 is an oblique implant, meaning it is dimensioned to be inserted into the disc space at an angle that is oblique to the midline of the disc space. For example, this implant insertion trajectory is common in a transforaminal lumbar interbody fusion (TLIF) surgical procedure. The implant 110 according to the alternative embodiment is similar in structure to the one described in FIGS. 1-15 in that it includes a housing 120, upper and lower endplates 130, 140, a wedge 150 and a drive mechanism 160 which are described in further detail below.

According to the embodiment of FIGS. 16-27, the implant 110 has a housing 120. The housing has the same structure as previously described, including a distal wall 124, a proximal wall 125 and first and second lateral walls 122, 123 extending between the distal and proximal walls 124, 125. The four walls define a hollow interior of the housing 120. However, the housing 120 according to the alternative embodiment is different in that the first lateral wall 122, the anterolateral wall when the implant 120 is positioned in the disc space, is greater in length than the second lateral wall 123 (the posterolateral wall). The distal wall 124 is tapered to aid in insertion of the implant 110 into the disc space. The proximal wall 125 includes a threaded drive screw aperture 127 and a graft delivery port 128. The drive screw aperture 127 is offset from the midline of the implant 110 and configured to receive the drive mechanism 160 therethrough. The height of the housing 120 is static, remaining unchanged when the implant 110 is in its collapsed configuration and its expanded configuration. The maximum height of the housing 120 is less than the maximum height of the overall implant 110.

Figure 23:
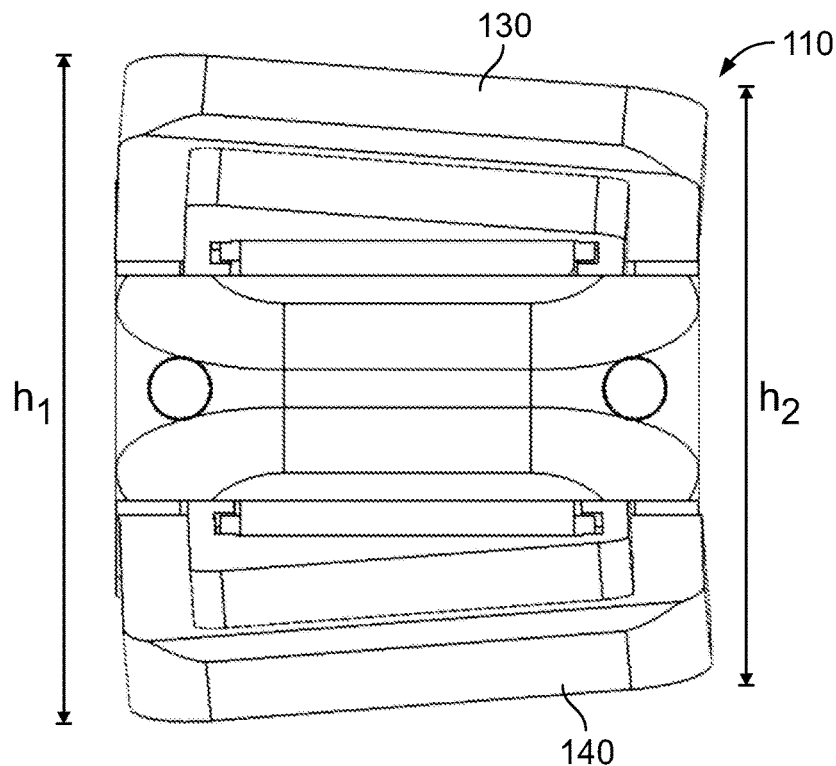
FIG. 23 is a front view of the expandable spinal fusion implant of FIG. 17.
Figure 24:
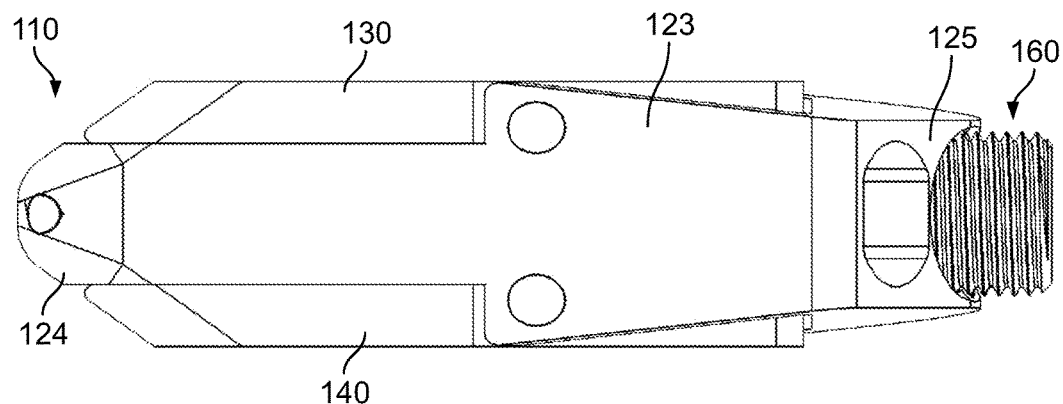
FIG. 24 is a first side view of the expandable spinal fusion implant of FIG. 16.
Figure 25:
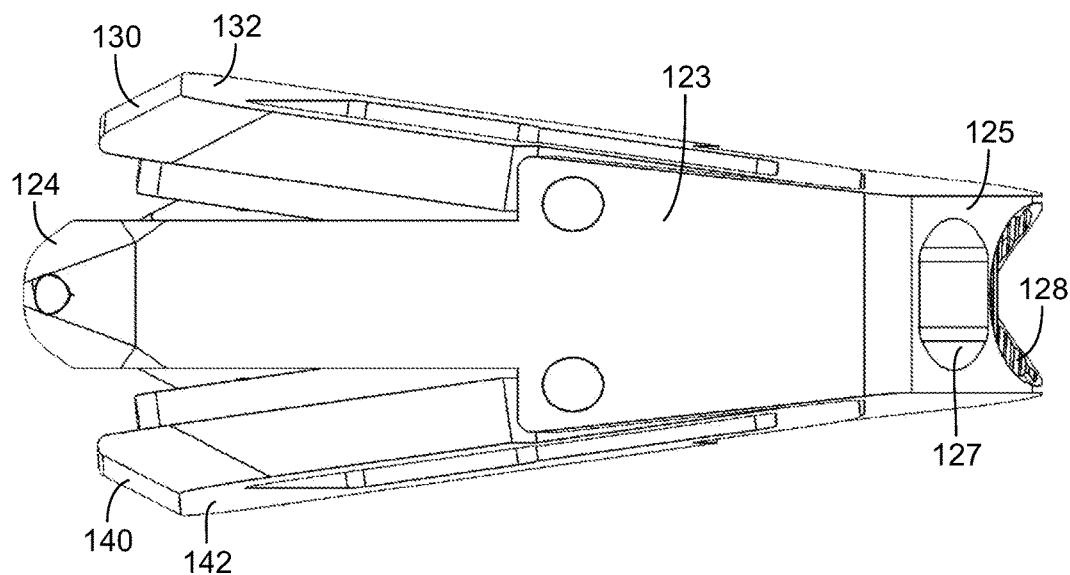
FIG. 25 is a first side view of the expandable spinal fusion implant of FIG. 17.
Figure 26:
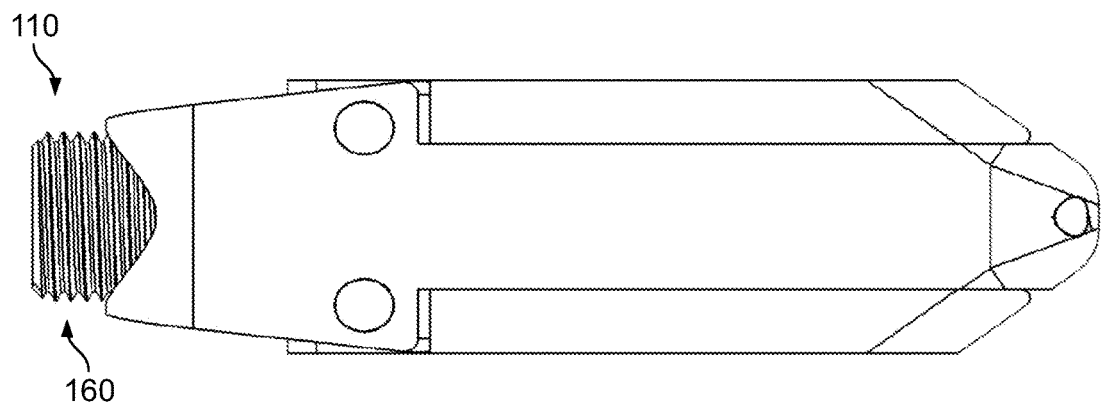
FIG. 26 is a second side view of the expandable spinal fusion implant of FIG. 16.
Figure 27:
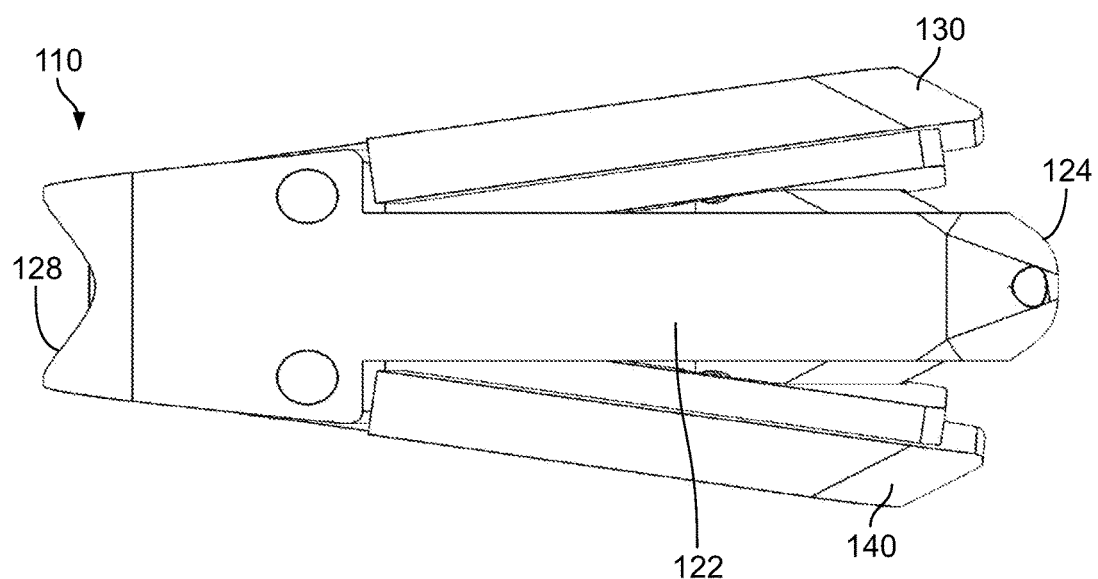
FIG. 27 is a second side view of the expandable spinal fusion implant of FIG. 17.
Figure 28:
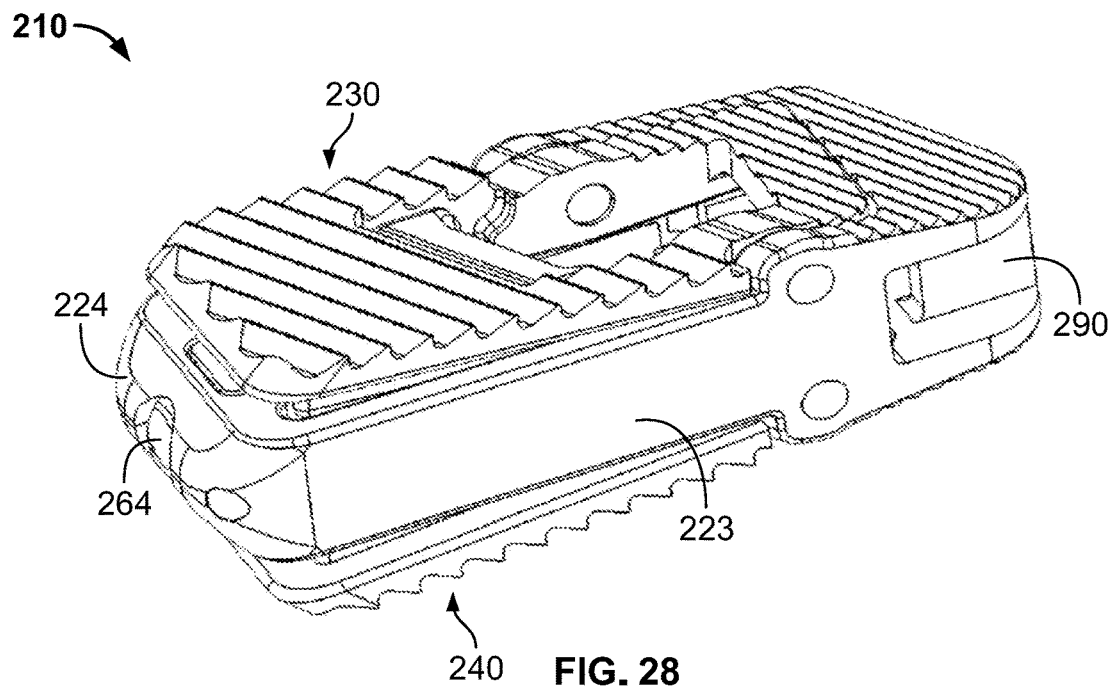
FIG. 28 is a perspective view of an expandable spinal fusion implant according to another alternative embodiment.
Figure 29:
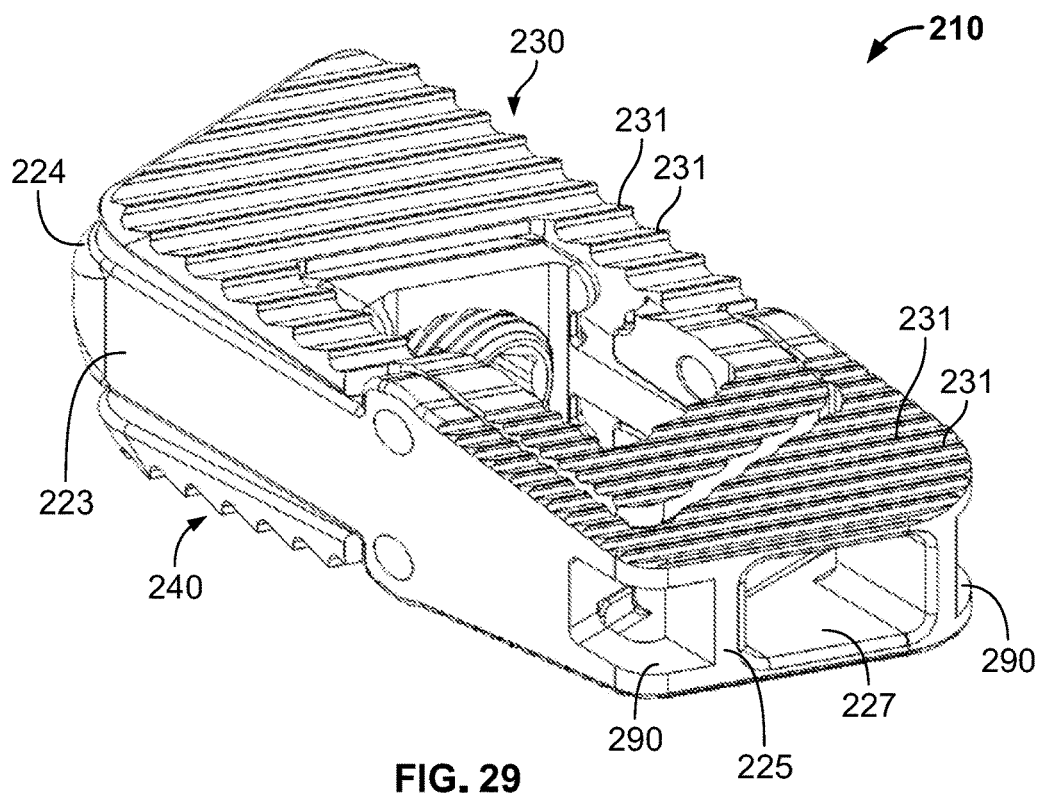
FIG. 29 is a rear perspective view of the expandable spinal fusion implant of FIG. 28.
Figure 30:
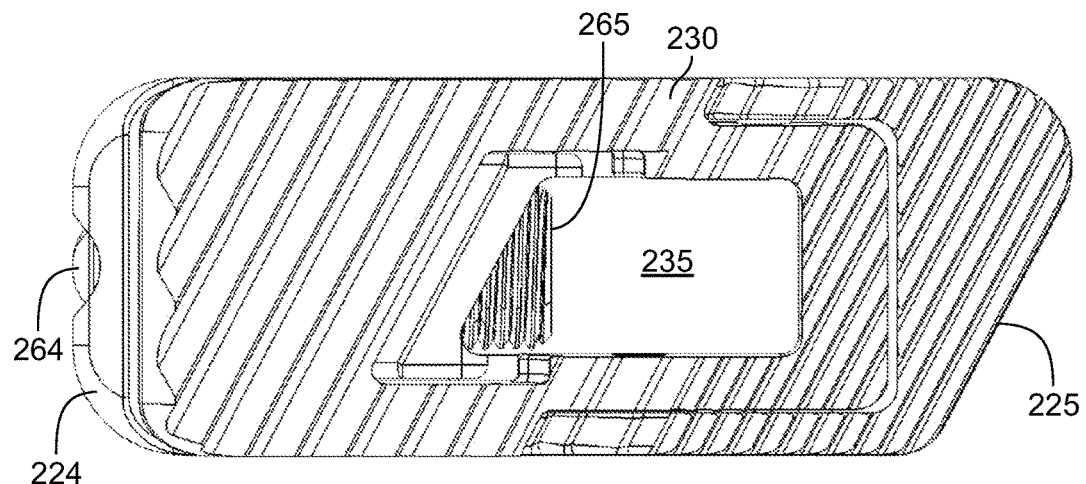
FIG. 30 is a top view of the expandable spinal fusion implant of FIG. 28.
Figure 31:
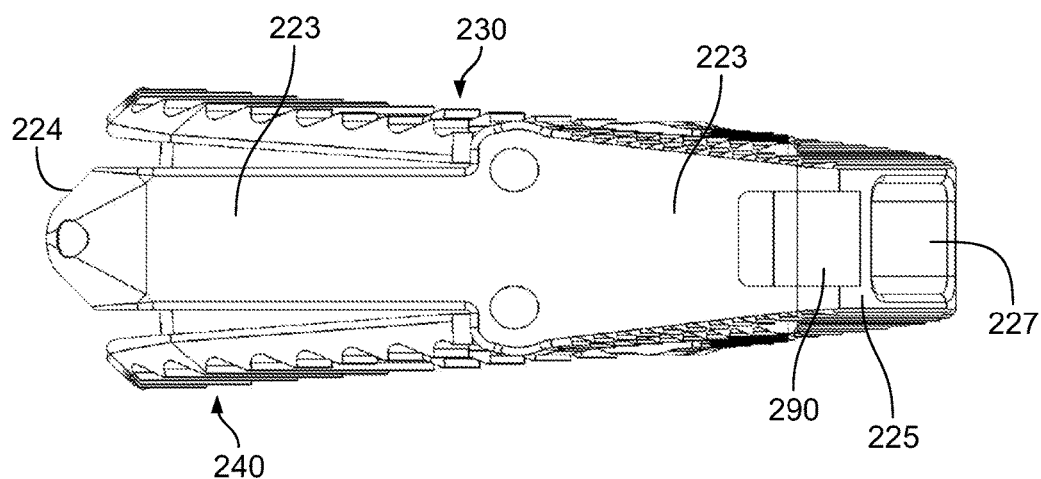
FIG. 31 is a first side view of the expandable spinal fusion implant of FIG. 28.
Figure 32:
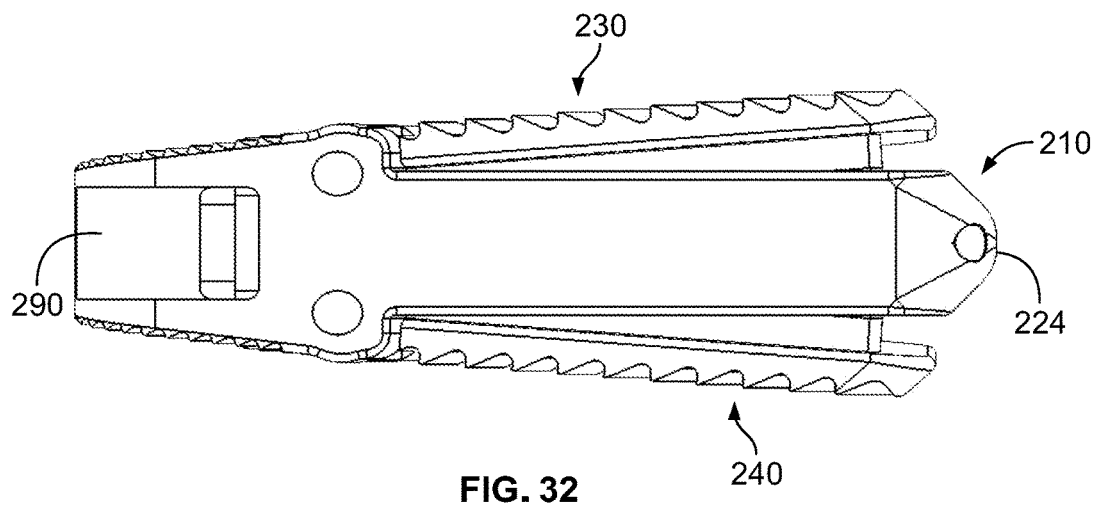
FIG. 32 is a second side view of the expandable spinal fusion implant of FIG. 28.

The upper and lower endplates 130, 140 according to this alternative embodiment are identical, mirror images of each other. The endplates 130, 140 of the alternative embodiment differ from the endplates 30, 40 of the previously described embodiment in that they increase in height across the endplate 130, 140 from the proximal end 133, 143 to the distal end 131, 141 of the endplate 130, 140 and from the posterolateral side 136, 146 to the anterolateral side 138, 148 of the endplate 130, 140. As a result, when the implant 120 is in its fully expanded configuration, the anterolateral height $h_1$ of the implant 110 is greater than the posterolateral height $h_2$ of the implant, as best shown in FIGS. 23 and 25. Each endplate 130, 140 further comprises a bone contacting surface 132, 142 and an interior surface 134, 144. Although not illustrated in FIGS. 16-27, it is contemplated that the bone contacting surfaces 132, 142 could include antimigration features. The interior surfaces 134, 144 of the endplates 130, 140 include a ramped surface 137, 147 at the distal end of the endplate 131, 141 that engage opposing angled surfaces 151, 152 on the wedge 150. According to the embodiment shown in FIGS. 16-27, the interior side surfaces of the endplates include slots 139, 149 for receiving projections 126 on the sides of the wedge 150.

According to the alternative embodiment, the wedge 150 is similar in structure to the wedge 50 as previously described. The wedge 150 has opposing angled surfaces 151, 152 at its distal end and a drive block 153 at its proximal end. The opposing angled surfaces 151, 152 and drive block 153 are coupled via a pair of lateral arms 154 defining a central aperture 155 therebetween. The drive block 153 similarly includes a graft aperture 157 through its thickness and a drive screw receptacle 158 dimensioned to house the distal end 164 of the drive screw 160.

The drive mechanism 160 of this alternative embodiment is similar in form and in function to the drive screw mechanism 60 described for the previous embodiment. The drive mechanism 160 is a drive screw. The drive screw 160 has a distal end 164 dimensioned to be received within the receptacle 158 of the drive block 153 and a proximal end 165 equipped with a mating feature for engaging a drive tool (not shown) and a threaded shaft 162 extending between the proximal end and distal end. As the drive screw 162 is rotated, the threads on the shaft 162 engage the complementary threads on the drive screw aperture 128 of the housing 120 allowing the drive screw to translate distally into the implant 110 thereby urging the wedge 150 distally within the implant and causing the endplates 130, 140 to separate.

FIGS. 28-36 illustrate yet another alternative embodiment of an expandable spinal fusion implant 210 in a partially expanded state. As with the embodiment illustrated in FIGS. 16-27, the current embodiment is designed to be an oblique implant for use in a TLIF procedure. The embodiment illustrated in FIGS. 28-36 includes the same basic structures as the two previous embodiments, including a housing 220, upper and lower endplates 230, 240, a wedge 250 and a drive mechanism 260. These structures are described in further detail in the following paragraphs.

According to the third embodiment of FIGS. 28-36, the implant 210 includes a housing 220. The housing 220 has a distal wall 224, a proximal wall 225 and first and second lateral walls 222, 223 defining a hollow interior. The distal wall 224 of the housing 220 is tapered from where it meets the lateral walls 222, 223 to the distal most point of the distal wall to aid in insertion of the implant 210 into the disc space. The distal wall 224 includes a drive mechanism aperture 228 configured to receive the distal end of the drive mechanism 260. The proximal wall 225 has first and second bone contacting surfaces 229 and a graft delivery port 227 extending through its thickness. The proximal wall 225 may also include channels 290 for receiving arms of an insertion tool (not shown) As illustrated in FIGS. 28-36, it is contemplated that the bone contacting surfaces 229 of the proximal wall 225 include anti-migration features 231, 241. The height of the housing 220 is static, remaining unchanged when the implant 210 is in its collapsed configuration and in its expanded configuration. The first lateral wall 222, the anterolateral wall of the implant when the implant is positioned within the disc space, has a length that is greater than the length of the second lateral wall 223 (the posterolateral wall). It is contemplated that the housing 220 can be manufactured of metal or PEEK.

Figure 33:
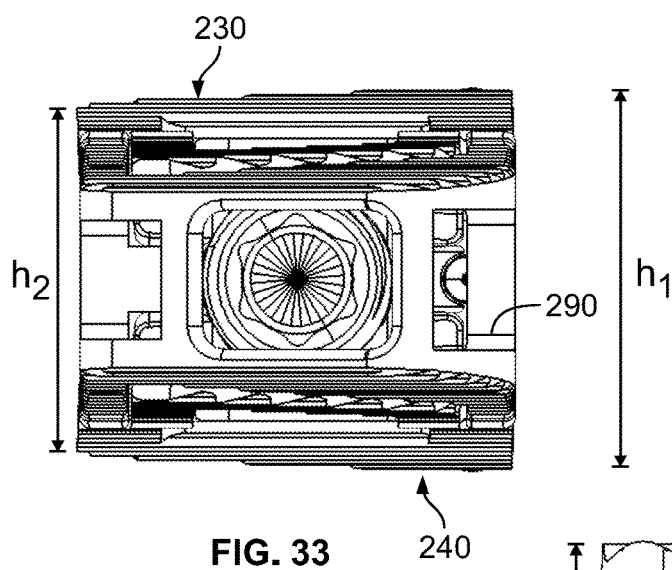
FIG. 33 is a back view of the expandable spinal fusion implant of FIG. 28.
Figure 34:
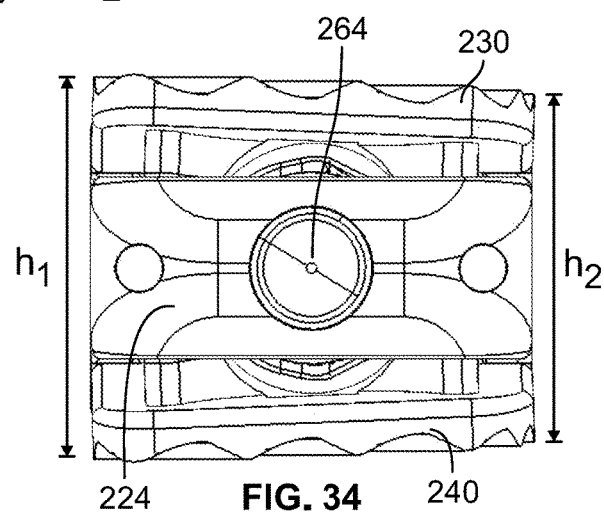
FIG. 34 is a front view of the expandable spinal fusion implant of FIG. 28.
Figure 35:
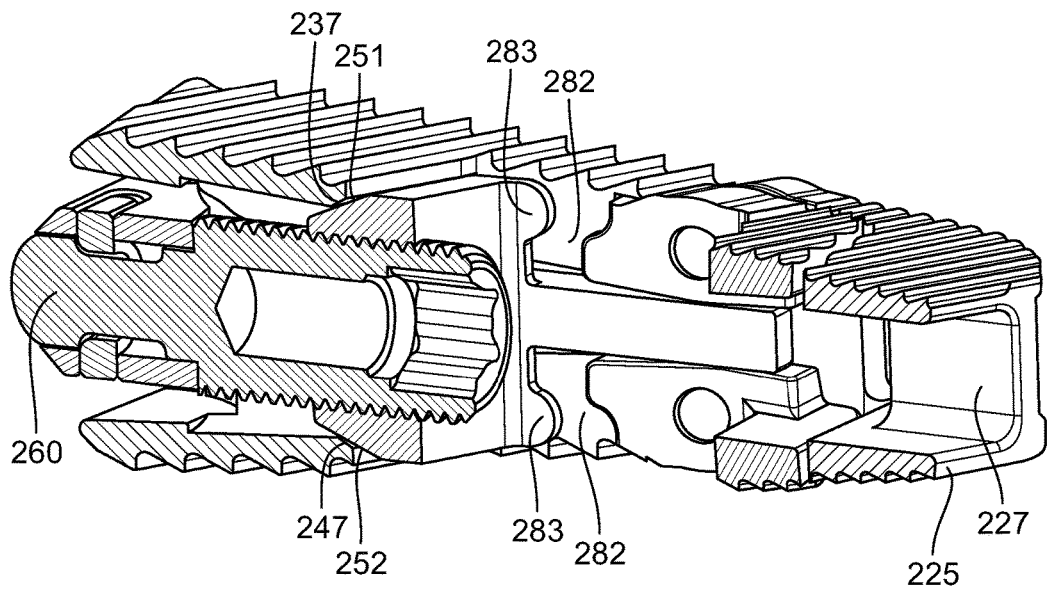
FIG. 35 is a perspective cross-sectional view of the expandable spinal fusion implant of FIG. 28.
Figure 36:
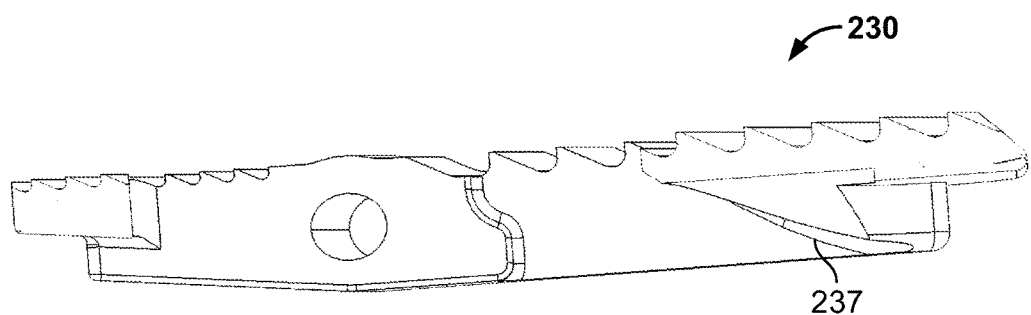
FIG. 36 is a side cross-sectional view of the upper endplate of the expandable spinal fusion implant of FIG. 28.

According to the embodiment shown in FIGS. 28-36, the housing is coupled to the upper and lower endplates 230, 240 via pins 239. The upper and lower endplates 230, 240 are identical, mirror images of each other. Each endplate 230, 240 has a bone contacting surface 232, 242 and an interior surface 234, 244. The bone contacting surfaces 232, 242 may include anti-migration features 239. The endplates 230, 240 include a central fusion aperture 235, 245 in communication with the hollow interior of the housing 220 to allow bone growth through the implant 210 after the implant has been placed within the disc space of patient. Each endplate 230, 240 further includes an interior side walls 272, 273 having a recess 282 and a projection 283 for engaging proximal projections 259 on the wedge 260. When the projections 283 on the interior side walls 272, 273 of the endplates are engaged with the proximal projections 259 on the wedge 250, the upper and lower endplates 230, 240 are locked in the collapsed configuration until such time as the wedge 260 is translated distally and the projections 283, 259 are disengaged. The interior surfaces 234, 244 of the endplates 230, 240 include a ramp 237, 247 adjacent the distal end of the endplates 230, 240 that engage the opposing angled surfaces 251, 252 on the wedge 250 to facilitate the expansion of the distal end 214 of the implant 210. As best illustrated in FIG. 36, the ramp 237, 247 is slightly radiused. While illustrated here as having a radiused ramp 237 and a generally planar angled surface 251, 252 on the wedge, it is contemplated that the ramp 237, 247 could be planar and the opposing angled surfaces 251, 252 on the wedge could be radiused. Alternatively, it is contemplated that both the ramp 237, 247 and the opposing angled surfaces 251, 252 could be planar or both could be radiused. As best seen in FIGS. 33 and 34, the endplates 230, 240 have a greater height on the anterolateral sides 232, 242 of the distal ends 234, 244 of the end plates such that when the implant is in its fully expanded state, the overall height of the implant is both greater at the distal end of the implant than at the proximal end of the implant but also the height $h_1$ on the anterolateral side of the implant is greater than the height $h_2$ on the posterolateral side of the implant.

The wedge 250 according to the third embodiment is housed in the hollow interior of the housing 220 and between the interior surfaces 234, 244 of the upper and lower endplates 230, 240. The wedge 250 has a distal face defined by opposing angled surfaces 251, 252 and a proximal face 293. The wedge has a threaded drive mechanism aperture 258 extending throughout the wedge from the proximal face 243 through the distal face dimensioned to receive a threaded shaft 262 of the drive mechanism 260. As previously mentioned, the wedge has projections 259 extending from the proximal face 293 for engaging projections 283 on the interior side walls 272, 273 of the endplates 230, 240. The wedge 250 is positioned in the interior of the implant 210 such that when the implant 210 is in its collapsed configuration the wedge 250 is sitting in the hollow interior and blocking the distal portion of the central fusion apertures 235, 245 of the endplates 230, 240. When the implant 210 is in its fully expanded configuration, the wedge has been urged distally and thus is blocking less of the central fusion apertures 235, 245 effectively increasing the size of the aperture extending through the implant 210.

According to the embodiment shown in FIGS. 28-36, the drive mechanism 260 includes a threaded shaft 262 having a proximal end 265 including an engagement feature 267 for mating with a drive tool (not shown). The distal portion 264 of the drive mechanism 260 extends distally from the threaded shaft 262 and is configured to be anchored in the distal wall 224 of the housing 220. The distal portion of the drive mechanism 260 is non-threaded, and is allowed to rotate within the drive mechanism aperture 227 in the distal wall 224 of the housing without translating. As the drive mechanism 260 is rotated by a drive tool, the threaded shaft engages complementary threads inside the threaded aperture 258 extending through the wedge 250 and causes the wedge 250 to translate distally until the implant 210 is fully expanded.

In use, the expandable spinal fusion implant 210 is inserted into a disc space between adjacent vertebral bodies in its collapsed configuration. Although not shown, it is contemplated that an insertion tool having two arms extending from the distal end will engage the insertion tool channels 290 on the proximal wall 225 of the housing 220. The insertion tool has a hollow shaft to allow the drive mechanism driver to be inserted therethrough. The distal end of the drive mechanism driver is inserted through the graft delivery port 227 in the housing 220 and engaged with the mating feature 267 of the drive mechanism 267. The drive mechanism driver is used to rotate the drive mechanism thereby causing the wedge 260 to translate distally between the upper and lower endplates 230, 240. Then the driver is disengaged from the drive mechanism and withdrawn from the hollow shaft of the insertion tool. Subsequently, graft material is inserted through the hollow shaft of the insertion tool, through the graft delivery port 227 in the proximal wall 224 of the housing 220 and into the hollow interior of the implant 210. In an exemplary embodiment, a sufficient amount of graft is inserted to fill the interior of the implant, through the central apertures 235, 245 in the endplates such that there is graft in compact contact with the endplates of each of the adjacent vertebral bodies.

A number of embodiments of the invention have been described. Nevertheless, it will be understood that various modifications may be made without departing from the spirit and scope of the invention. Accordingly, other embodiments are within the scope of the following claims.

What is claimed is:

1. An expandable spinal fusion implant, comprising:
a housing having a first endwall, a second endwall, a first sidewall, and a second sidewall defining a hollow interior, wherein an overall length of the first sidewall is greater than an overall length of the first endwall;
an upper endplate and a lower endplate, the upper endplate having a first bone contacting surface and a first interior surface including a first ramp, the lower endplate having a second bone contacting surface and a second interior surface including a second ramp;
a wedge positioned within the hollow interior of the housing and between the first interior surface and second interior surface, the wedge including a first angled surface that engages the first ramp and a second angled surface that engages the second ramp; and
a drive mechanism in contact with the first endwall and the wedge, wherein the drive mechanism is configured to drive the wedge in a direction toward the first endwall such that the first angled surface of the wedge engages the first ramp and the second angled surface of the wedge engages the second ramp, moving the upper endplate and lower endplate from a collapsed configuration to an expanded configuration, wherein in the expanded configuration the implant has a maximum height adjacent the first endwall that is greater than a maximum height adjacent the second endwall, and wherein, in the expanded configuration, the implant has a maximum height adjacent the first sidewall that is greater than a maximum height adjacent the second sidewall and the maximum height adjacent the second endwall is a fixed non-adjustable height equal to a maximum height of the second endwall of the housing.

2. The implant of claim 1, wherein a height of the housing is static.

3. The implant of claim 1, wherein a height of the upper endplate increases in a first direction across the upper endplate towards the first endwall and parallel to the first sidewall, and also increases in a second direction across the upper endplate towards the first sidewall and parallel to the first endwall.

4. The implant of claim 3, wherein a height of the lower endplate increases in the first direction across the lower endplate towards the first endwall and parallel to the first sidewall, and in the second direction across the lower endplate towards the first sidewall and parallel to the first endwall.

5. The implant of claim 1, wherein the first sidewall has a length that is greater than a length of the second sidewall.

6. The implant of claim 1, wherein the housing includes a static upper surface forming a third bone contacting surface which faces upward and extends from adjacent the second endwall to a position adjacent to the first bone contacting surface of the upper endplate, and the housing includes a static lower surface forming a fourth bone contacting surface which faces downward and extends from adjacent the second endwall to a position adjacent to the second bone contacting surface of the lower endplate, wherein in the expanded configuration the third bone contacting surface is co-planar with the first bone contacting surface of the upper endplate, and in the expanded configuration the fourth bone contacting surface is co-planar with the second bone contacting surface of the lower endplate.

7. The implant of claim 6, wherein the drive mechanism engages with the first endwall and the second endwall is free of the drive mechanism.

8. The implant of claim 7, wherein the upper endplate includes a first opening and the lower endplate includes a second opening such that a fusion aperture extends through the hollow housing between the upper and lower endplates.

9. The implant of claim 8, wherein the fusion aperture is situated closer to the second endwall than the wedge.

10. The implant of claim 9, wherein the wedge defines a wall of the fusion aperture such that the size of the fusion aperture increases as the implant is moved from the collapsed configuration to the expanded configuration.

11. The implant of claim 1, wherein the first ramp has a radiused surface and the second ramp has a radiused surface.

12. The implant of claim 11, wherein the first angled surface has a planar surface and the second angled surface has a planar surface.

13. The implant of claim 1, wherein the drive mechanism includes a shaft with a first end rotatably coupled to the first endwall and a second end threadedly coupled to the wedge.

14. The implant of claim 13, wherein the second end of the shaft of the drive mechanism is free of the second endwall.

15. The implant of claim 1, wherein a distal end of the housing is tapered.

16. The implant of claim 1, wherein the drive mechanism comprises a drive screw.

17. The implant of claim 1, wherein the second endwall comprises a drive screw aperture.

18. The implant of claim 1, wherein the second endwall comprises a graft delivery port.

19. The implant of claim 1, wherein the second endwall comprises a channel configured to receive at least a portion of an insertion tool.

20. The implant of claim 1, wherein the implant is configured for use in a transforaminal lumbar interbody fusion surgical procedure.

* * * * *